United States Patent
Sidebotham et al.

(10) Patent No.: US 10,863,993 B2
(45) Date of Patent: Dec. 15, 2020

(54) SYSTEM AND METHOD FOR PREPARING PROSTHETIC HIP IMPLANTATION

(71) Applicants: Christopher G. Sidebotham, Mendham, NJ (US); Leon Roitburg, East Hanover, NJ (US); Randall J. Lewis, Bethesda, MD (US)

(72) Inventors: Christopher G. Sidebotham, Mendham, NJ (US); Leon Roitburg, East Hanover, NJ (US); Randall J. Lewis, Bethesda, MD (US)

( * ) Notice: Subject to any disclaimer, the term of this patent is extended or adjusted under 35 U.S.C. 154(b) by 182 days.

(21) Appl. No.: 15/835,381

(22) Filed: Dec. 7, 2017

(65) Prior Publication Data

US 2018/0098776 A1 Apr. 12, 2018

Related U.S. Application Data

(63) Continuation-in-part of application No. 14/065,327, filed on Oct. 28, 2013, now abandoned, which is a
(Continued)

(51) Int. Cl.
*A61B 17/00* (2006.01)
*A61B 17/16* (2006.01)
(Continued)

(52) U.S. Cl.
CPC .......... *A61B 17/1615* (2013.01); *A61B 17/16* (2013.01); *A61B 17/1659* (2013.01);
(Continued)

(58) Field of Classification Search
USPC ........................................................... 606/80
See application file for complete search history.

(56) References Cited

U.S. PATENT DOCUMENTS

| | | |
|---|---|---|
| 499,619 A | 6/1893 | Weed |
| 1,916,874 A | 7/1933 | Wilhelm |

(Continued)

FOREIGN PATENT DOCUMENTS

| | | |
|---|---|---|
| DE | 10 2005 058 107 | 7/2007 |
| EP | 2 359 755 | 8/2011 |

OTHER PUBLICATIONS

International Search Report from PCT Application No. PCT/US2013/021473 dated Jun. 20, 2013.
(Continued)

*Primary Examiner* — Sameh R Boles
(74) *Attorney, Agent, or Firm* — Klarquist Sparkman, LLP

(57) ABSTRACT

A system is provided for preparing prosthetic hip implantation. The system includes a first broach, a second broach, and a trial neck having a body portion and a neck portion. A proximal end of the first broach comprises a first base having a first maximum area. The body portion can be releasably coupled to the proximal end of the first broach so as to define a first offset between a medial end of the neck portion and a longitudinal axis of the first broach, or releasably coupled to the proximal end of the second broach so as to define a second offset between the medial end of the neck portion and a longitudinal axis of the second broach. The first offset is smaller than the second offset.

8 Claims, 22 Drawing Sheets

Related U.S. Application Data continuation of application No. 13/741,211, filed on Jan. 14, 2013, now Pat. No. 9,101,368.

(60) Provisional application No. 61/586,685, filed on Jan. 13, 2012.

(51) Int. Cl.
| | |
|---|---|
| *B23K 26/00* | (2014.01) |
| *B23P 15/46* | (2006.01) |
| *A61F 2/46* | (2006.01) |
| *A61B 17/92* | (2006.01) |
| *A61F 2/36* | (2006.01) |

(52) U.S. Cl.
CPC ...... *A61B 17/1666* (2013.01); *A61B 17/1668* (2013.01); *A61F 2/4684* (2013.01); *B23K 26/0093* (2013.01); *B23P 15/46* (2013.01); *A61B 17/164* (2013.01); *A61B 17/1677* (2013.01); *A61B 17/921* (2013.01); *A61B 2017/00526* (2013.01); *A61B 2017/922* (2013.01); *A61F 2/36* (2013.01); *A61F 2/3609* (2013.01)

(56) References Cited

U.S. PATENT DOCUMENTS

| | | |
|---|---|---|
| 4,116,200 A | 9/1978 | Braun et al. |
| 4,598,447 A | 7/1986 | Whyde |
| 5,501,686 A | 3/1996 | Salyer |
| 5,709,688 A | 1/1998 | Salyer |
| 5,968,049 A | 10/1999 | Da Rold |
| 6,318,651 B1 | 11/2001 | Spiering |
| 6,764,490 B1 | 7/2004 | Szabo |
| 7,220,264 B1 | 5/2007 | Hershberger |
| 8,784,422 B2 | 7/2014 | Lechot et al. |
| 8,834,471 B2 | 9/2014 | Roger et al. |
| 2003/0135219 A1 | 7/2003 | Salyer et al. |
| 2003/0181916 A1 | 9/2003 | Wolford |
| 2004/0225294 A1 | 11/2004 | Frederick et al. |
| 2005/0059974 A1 | 3/2005 | Wolford et al. |
| 2005/0075639 A1 | 4/2005 | Lechot |
| 2005/0113837 A1 | 5/2005 | Salyer |
| 2006/0095041 A1 | 5/2006 | Fehlbaum et al. |
| 2006/0217730 A1 | 9/2006 | Termanini |
| 2007/0162033 A1* | 7/2007 | Daniels ............... A61B 17/162 606/80 |
| 2008/0195105 A1* | 8/2008 | Sidebotham ....... A61B 17/1617 606/80 |
| 2008/0215159 A1 | 9/2008 | Stamp |
| 2008/0306482 A1 | 12/2008 | Muller |
| 2010/0069908 A1 | 3/2010 | Sidebotham et al. |
| 2010/0145342 A1 | 6/2010 | Grace et al. |
| 2011/0202060 A1 | 8/2011 | White et al. |

OTHER PUBLICATIONS

Written Opinion of the International Search Authority from PCT Application No. PCT/US2013/021473 dated Jun. 20, 2013.

* cited by examiner

PRESS FIT ACETABULAR IMPLANT AS PART OF A TOTAL HIP PROCEDURE
ACETABULAR IMPLANT

PREPARATION OF THE ACETABULUM

ACETABULAR REAMER
HOLLOW SPHERICAL CUTTER

CUTTING TOOTH
GEOMETRY SHOWN

CUTTING TOOTH HEIGHT SET

CUTTING TEETH ZONES BASED ON FUNCTION
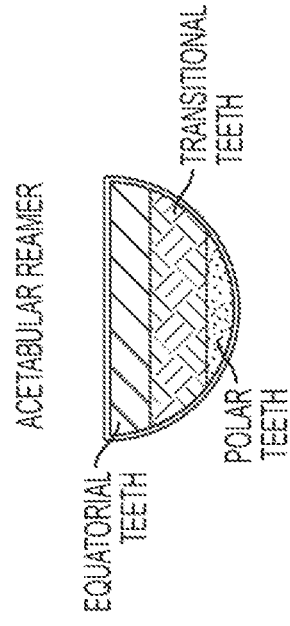
ACETABULUM UNDERSIZED TO REAMER BY ONE (1)mm
FIG. 7A
ACETABULAR REAMER
EQUATORIAL TEETH — POLAR TEETH — TRANSITIONAL TEETH
FIG. 7B
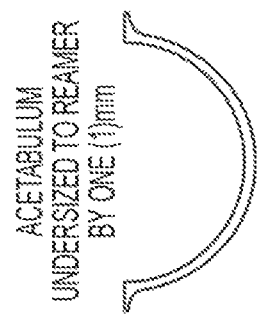
INITIATION OF REAMING TEETH ARE PRIMARILY SIDE CUTTING
FIG. 7C
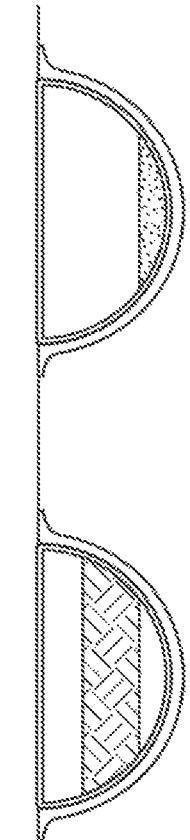
REAMER INTRODUCED APPROXIMATELY 50% TEETH ARE TRANSITIONING FROM SIDE CUTTING TO END CUTTING
FIG. 7D
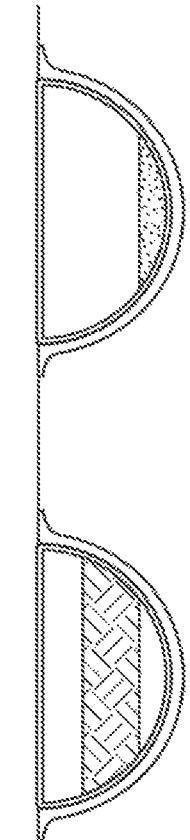
REAMER INTRODUCED 100% TEETH ARE PRIMARILY END CUTTING
FIG. 7E

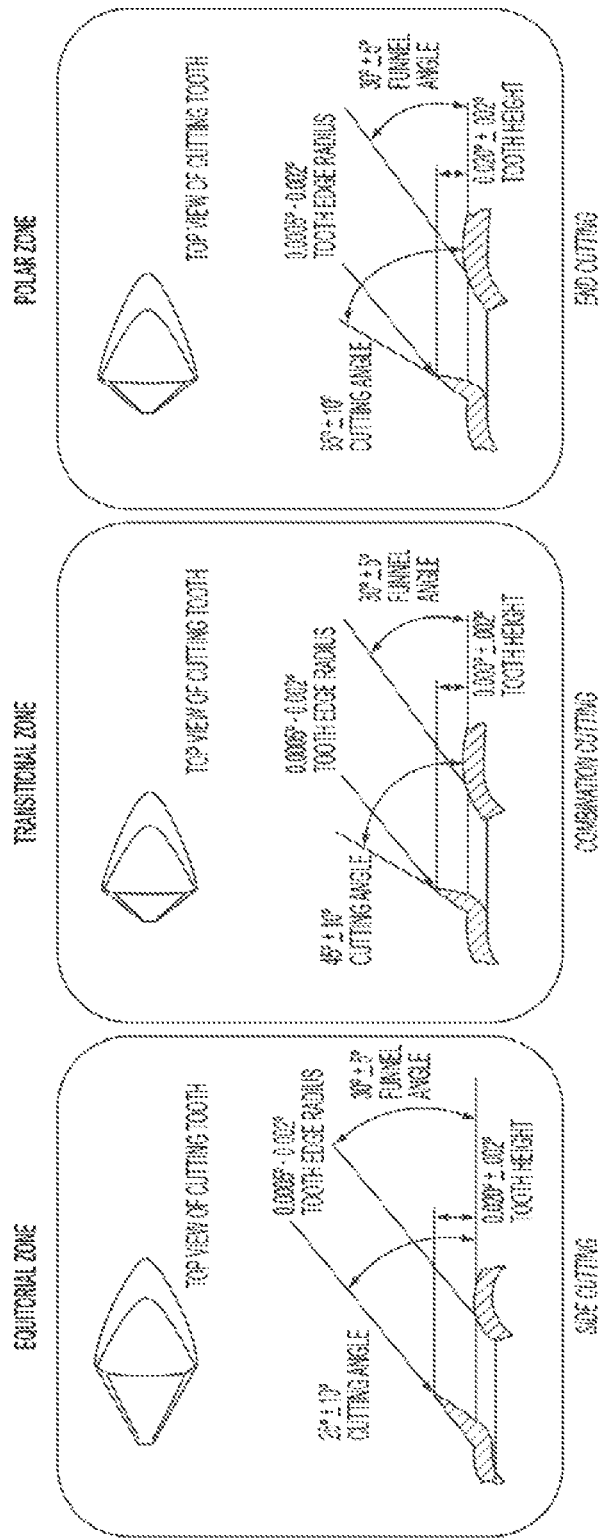

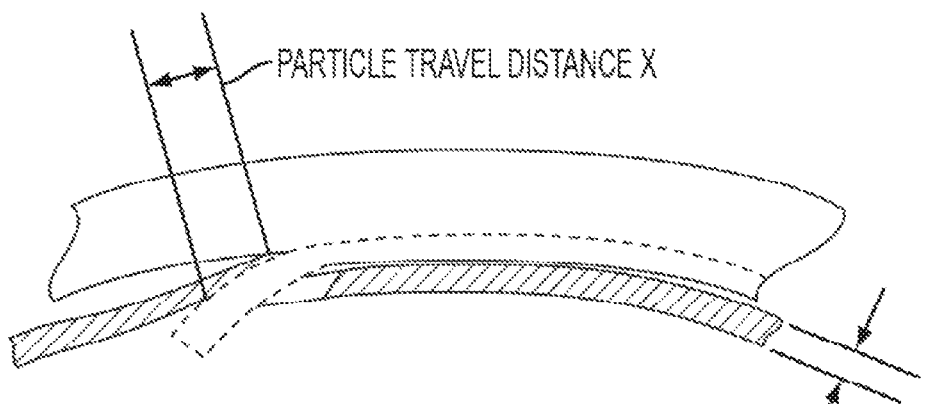
FIG. 10A .005" - .020" (0.13 - 0.51mm)
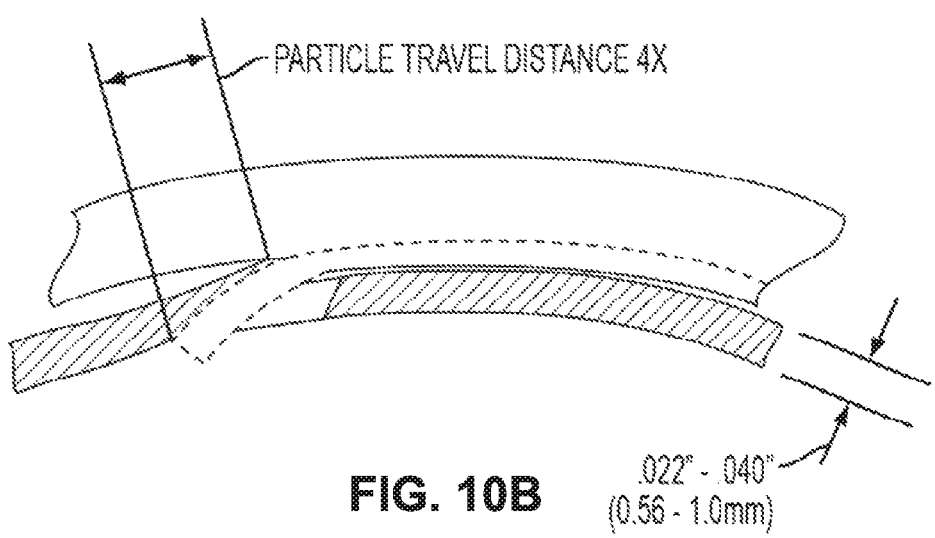
FIG. 10B .022" - .040" (0.56 - 1.0mm)

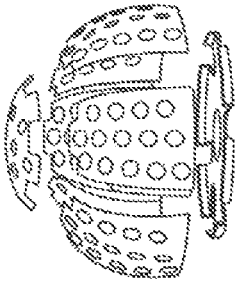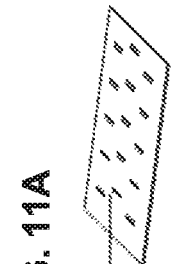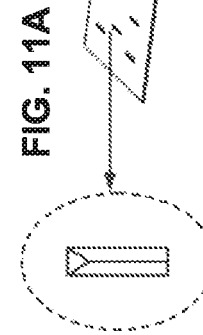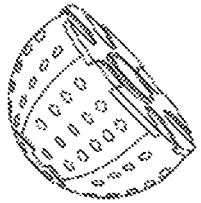

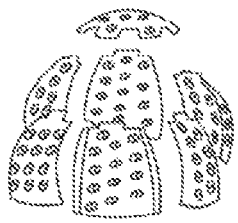

STAMPED CUTTING
PANELS

FIG. 16A

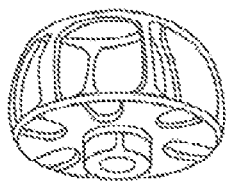

INJECTION MOLDING TOOL
CREATES PLASTIC FRAME
AROUND PANELS

FIG. 16B

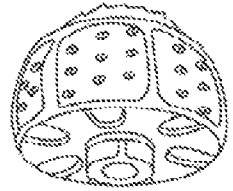

FINISHED REAMER IS STRUCTURALLY
SOUND THROUGH THE FRAME AND
MAINTAINS CUTTER SPHERICITY AND
TOLERANCES WITHIN .004"

FIG. 16C

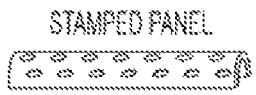

STAMPED PANEL FIG. 17A

MOLDED PLASTIC FRAME FIG. 17B

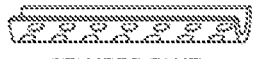

STAMPED PANEL FIG. 17C

FIG. 17D

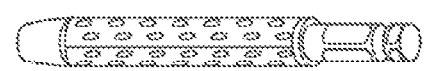

FINISHED REAMER IS STRUCTURALLY
SOUND THROUGH THE FRAME AND
MAINTAINS CUTTER CONCENTRICITY
AND TOLERANCES WITHIN .004"

Hollow Spherical Reamers:
*Acetabulum Preparation*

Hollow Tapered Reamers:
*Intramedullary Canal of Bones*

Hollow Cylindrical Reamers:
*Intramedullary Canal of Bones*

Hollow Flat Reamers:
*Patella Articular Surface*

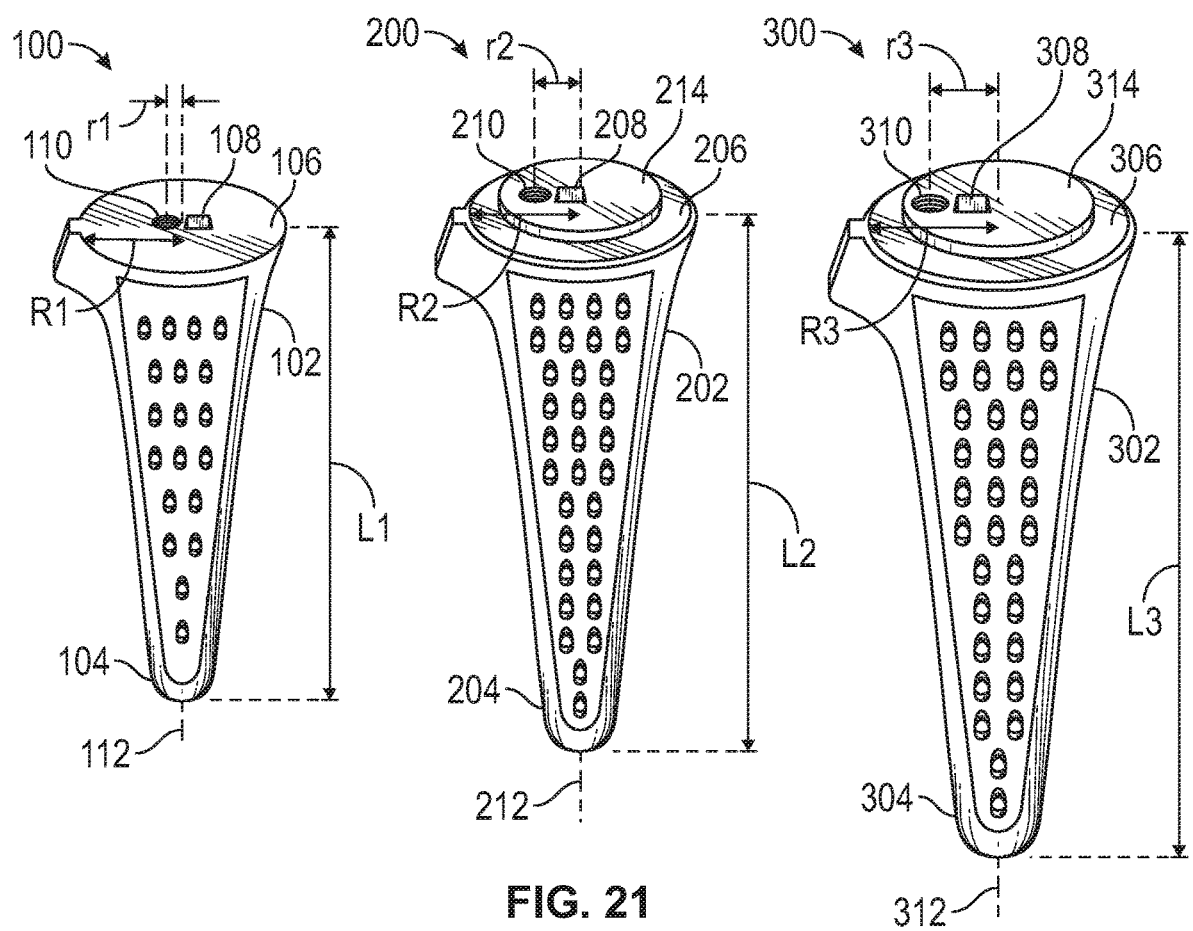
FIG. 21
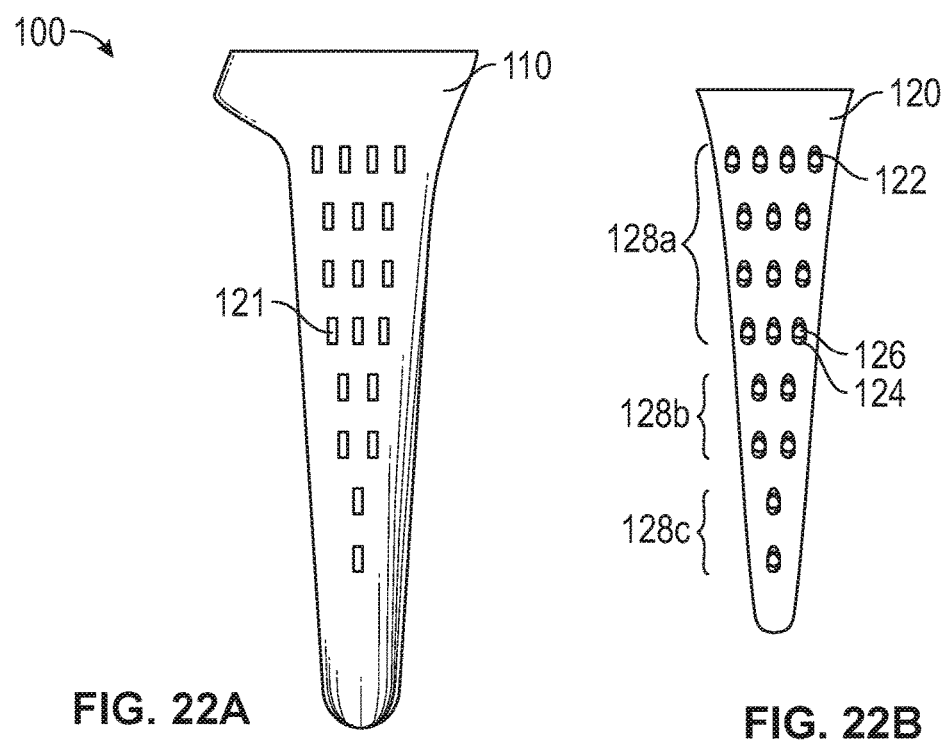
FIG. 22A
FIG. 22B

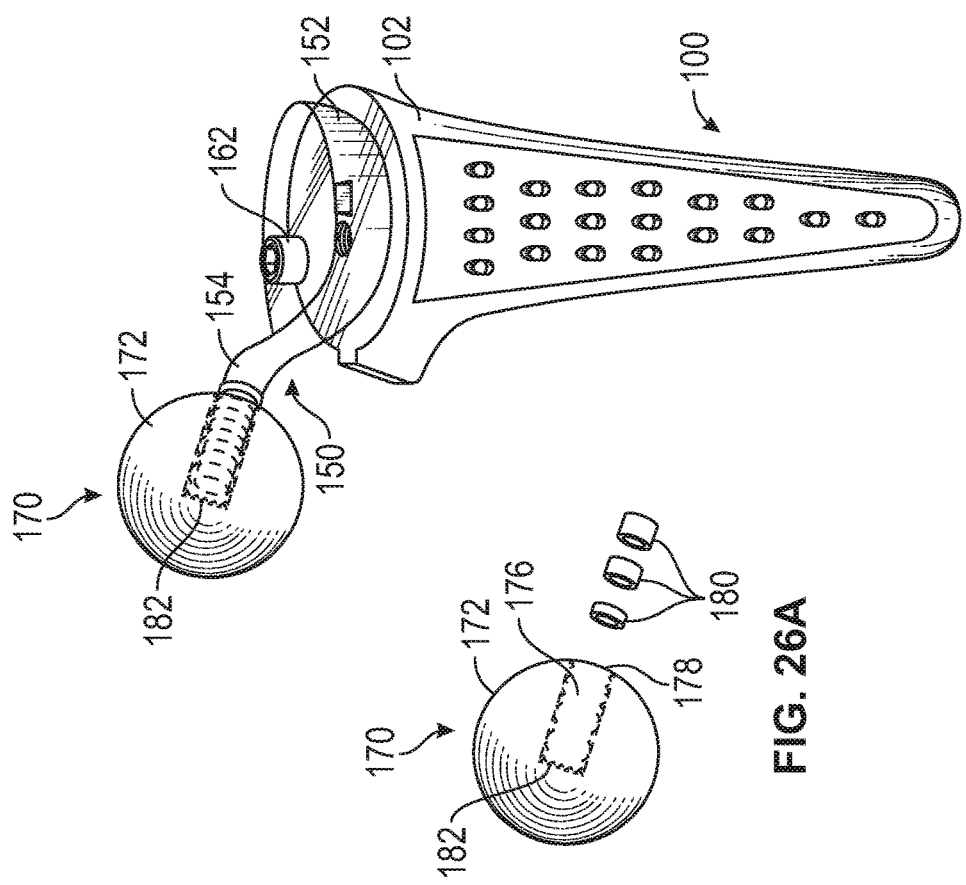
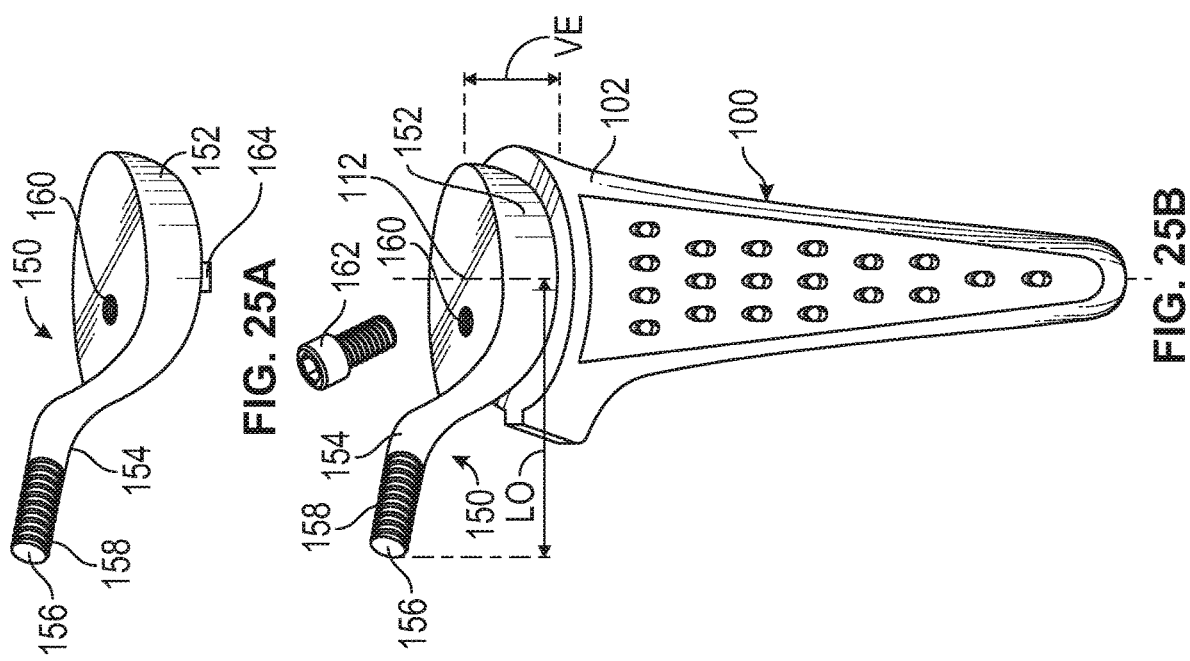
FIG. 26B
FIG. 26A
FIG. 25A
FIG. 25B

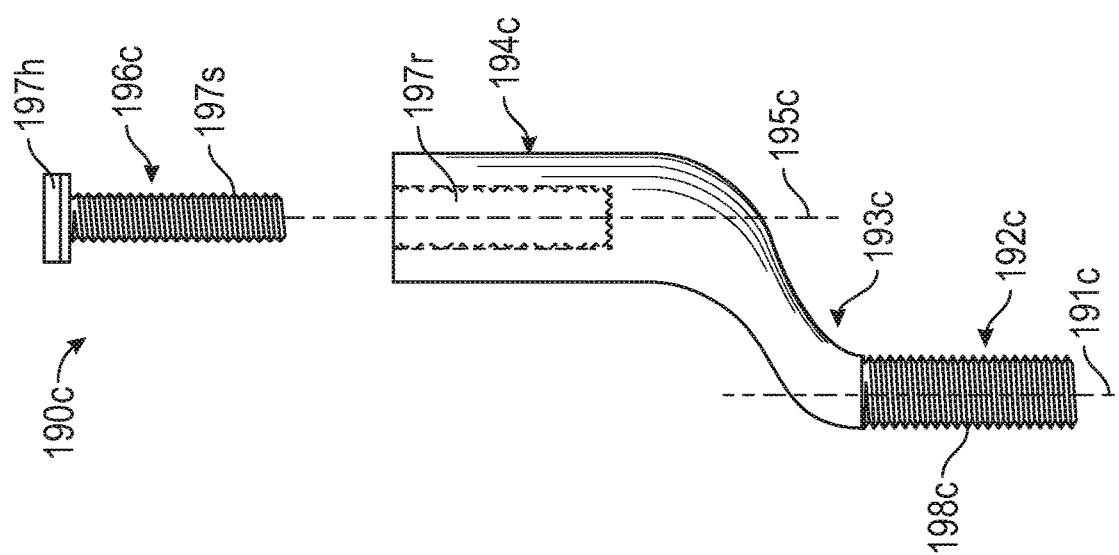
FIG. 27C
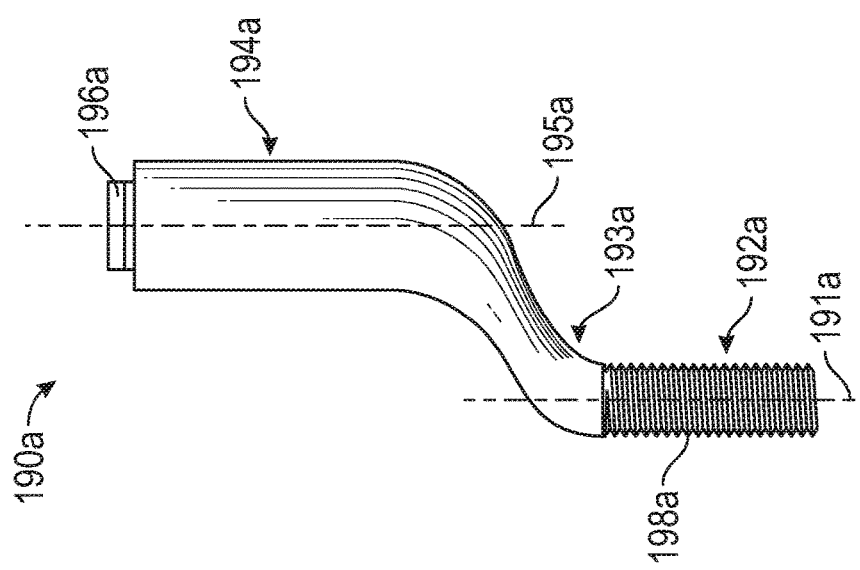
FIG. 27B
FIG. 27A

SYSTEM AND METHOD FOR PREPARING PROSTHETIC HIP IMPLANTATION

CROSS REFERENCE TO RELATED APPLICATION

This is a continuation-in-part of U.S. application Ser. No. 14/065,327, filed Oct. 28, 2013, which is a continuation of U.S. application Ser. No. 13/741,211, filed Jan. 14, 2013, now U.S. Pat. No. 9,101,368, which claims the benefit of U.S. Provisional Application No. 61/586,685, which was filed on Jan. 13, 2012, and are incorporated herein by reference in their entirety.

FIELD

This disclosure relates to novel systems and methods relating to orthopedic surgery, and more specifically, preparation of prosthetic hip implantation.

BACKGROUND

Cutting tools, such as medical reamers used by surgeons, generally have a cutting surface that is able to cut and/or remove material from an object. For example, in many different disciplines in orthopedics cutting tools are used for machining bone in the preparation of artificial joints including hips, knees, elbows and shoulders, and also in the repair of long bone fractures. The design and method of manufacturing cutting surfaces of cutting tools can affect the efficiency, functional life of the spherical reamer and cost in manufacturing. Accordingly, improvements relating to design and manufacturing methods are desirable.

Moreover, insertion of a hip prosthesis entails many surgical steps and requires multiple, often heavy sets of reusable instruments, generally contained in previously sterilized trays. The sterilization, unpacking, checking for completeness and sterility and sorting for use during surgery are time consuming, generating significant costs for personnel time and essentially non-productive operating room time. Thus, improvements relating to systems and methods for preparing prosthetic hip implantation are desirable.

SUMMARY

Disclosed herein are exemplary embodiments of devices, systems, and related methods for performing orthopedic surgery. In some implementations, the devices and systems can be used to preparing a prosthetic hip implantation. In some embodiments, the devices and systems can be included in a sterile kit. In some embodiments, some of the devices can be disposable.

In some embodiments, improved cutting tools and methods of manufacturing the same are provided.

In certain implementations, the cutting tools can comprise medical reamers, including acetabular reamers, long bone cylindrical reamers, long bone tapered reamers, patella reamers and glenoid reamers along with the design of different cutting teeth in specific zones of the reamers and the improved method of making these reamers and their cutting edges.

In some implementations, a cutting tool is provided with a cutting surface on a first side of the cutting tool and an attachment member on a second side of the cutting tool. The cutting surface can include a plurality of cutting edges and the attachment member can be configured to be coupled to a powered driving member (e.g., a drill). The cutting tool can comprise an axis of rotation and the cutting surface can define a plurality of latitude lines. The plurality of cutting edges can be oriented at varying orientation angles relative to the latitude lines.

In some implementations, the plurality of cutting edges can be increased to three or more different zones and respective cutting edges in the different zones have different characteristics. The different zones can comprise a polar zone, a transition zone, and an equatorial zone. Respective cutting edges can define a cutting angle between the cutting edge and a first side of the cutting tool, and the cutting angle between cutting edges in the polar zone can be larger than those defined by cutting edges in the transition zone, and the cutting angle between cutting edges in the transition zone can be larger than those defined by cutting edges in the equatorial zone. In some implementations, the tooth height can be the same (i.e., substantially the same) regardless of the cutting angle.

In some implementations, the orientation angles can vary depending on whether the respective cutting edges are in the polar zone, the transition zone, or the equatorial zone, and the orientation angle of respective cutting edges in the equatorial zone is greater than the orientation angle of respective cutting edges in the transition zone, and the orientation angle of respective cutting edges in the transition zone is greater than the orientation angle of respective cutting edges in the polar zone.

In some implementations, the thickness of the side wall can be less than 0.040 inches, or in some cases, between 0.022 inches and 0.040 inches. Openings can be provided adjacent respective cutting edges, the respective openings defining a funnel angle that is between 20 and 40 degrees. In some cases, the funnel angle can be between 25 and 35 degrees.

In some implementations, the cutting surface can be a panel and the cutting tool can comprise a plurality of separate panels. The cutting tool can include a frame member (e.g., a center support and a base) and the plurality of separate panels can be coupled to the frame member.

In another implementation, a method for forming a cutting tool is provided. The method can include forming a plurality of panels from one or more flat sheets of metal and coupling the plurality of panels to a frame member to form the cutting tool. The plurality of panels can be formed with a plurality of cutting edges and a plurality of openings adjacent respective cutting edges. When coupled to the frame member, the plurality of panels can define a plurality of latitude lines about the axis of rotation of the cutting tool and the plurality of formed cutting edges have orientation angles relative to the latitude lines that vary. In some cases, respective panels can have cutting edges with orientation angles that vary along the respective panel.

In certain implementations, the act of forming a plurality of panels can comprise stamping the one or more flat sheets of metal to form a plurality of cavities and punching holes at or adjacent to the plurality of cavity to provide bone-chip-receiving openings. The act of forming the plurality of cavities can include forming a plurality of "V"-shaped cavities.

In certain implementations, the act of forming the plurality of panels can include stamping the one or more panels to create a desired height of the cutting edges and to provide a desired curvature of the one or more panels.

In certain implementations, the act of coupling the plurality of panels to the frame member can include forming a frame member that comprises a center support, a base, and a form dome, and securing the plurality of panels to the center support, the base, and the form dome. In some cases, the act of securing the plurality of panels to the center support, the base, and the form dome can be performed by laser welding or other types of welding. The act of coupling the plurality of panels to the frame member can also include placing the plurality of panels into an injection molding tool and injection molding the frame member around the plurality of panels to create the frame member.

In some implementations, the act of forming a plurality of panels from one or more flat sheets of metal can include forming the plurality of cutting edges with different zones that have cutting edges with different characteristics, the different zones comprising a polar zone, a transition zone, and an equatorial zone. Respective cutting edges can define a cutting angle between the cutting edge and a first side of the cutting tool, and the cutting angle between cutting edges in the polar zone can be larger than those defined by cutting edges in the transition zone, and the cutting angle between cutting edges in the transition zone can be larger than those defined by cutting edges in the equatorial zone.

In certain implementations, the act of punching holes at or adjacent to the plurality of cavity can comprise forming bone-chip-receiving openings with a funnel angle that is between 20 and 40 degrees. In addition, in some cases, the one or more flat sheets of metal can have a thickness less than 0.040 inches.

In certain implementations, the method can include determining an effective functional life of the cutting tool.

In other embodiments, a cutting tool is provided that can have a cutting surface on a first side of the cutting tool, the cutting surface comprising a plurality of cutting edges, and an attachment member on a second side of the cutting tool, the attachment member being configured to be coupled to a powered driving member. A plurality of cutting edges can be provided in different zones and respective cutting edges in the different zones can have different characteristics.

Certain embodiments of the disclosure also concern a system for preparing prosthetic hip implantation. The system can include one or more broaches and a trial neck. Each broach can have a proximal end and a distal end. The trial neck can have a body portion and a neck portion extending medially from the body portion. Each broach can define a longitudinal length measured between the proximal and distal ends of the broach. The longitudinal length of a second broach can be larger than the longitudinal length of a first broach. The body portion of the trial neck can be releasably coupled to the proximal end of the first broach so as to define a first offset between a medial end of the neck portion and a longitudinal axis of the first broach. The body portion of the trial neck can be releasably coupled to the proximal end of the second broach so as to define a second offset between the medial end of the neck portion and a longitudinal axis of the second broach. The first offset can be smaller than the second offset.

In some embodiments, the proximal end of the first broach can comprise a first base. A radial cross-sectional area of the first broach can progressively increase from the distal end of the first broach to the first base which has a first maximum area. The proximal end of the second broach can comprise a second base. A radial cross-sectional area of the second broach can progressively increase from the distal end of the second broach to the second base which has a second maximum area. The second maximum area can be larger than the first maximum area.

In some embodiments, the proximal end of the first broach can comprise a first opening above a first longitudinal lumen in the first broach. The proximal end of the second broach can comprise a second opening above a second longitudinal lumen in the second broach. A first radial offset measured between the first opening to the longitudinal axis of the first broach can be smaller than a second radial offset measured between the second opening to the longitudinal axis of the second broach.

In some embodiments, a ratio of the first radial offset to a maximum radial dimension of the first base can be smaller than a ratio of the second radial offset to a maximum radial dimension of the second base.

In some embodiments, the proximal end of the first broach can comprise a first platform extending proximally relative to the first base. The proximal end of the second broach can comprise a second platform extending proximally relative to the second base. The second platform can be higher than the first platform along the longitudinal axis of respective broaches.

In some embodiments, a height of the first platform can range between 0 mm and about 5 mm.

In some embodiments, the first base can top the proximal end of the first broach, and the proximal end of the second broach can comprise a platform extending more proximally relative to the second base.

In some embodiments, the body portion of the trial neck can comprise a channel extending longitudinally through the body portion. The channel can be configured to selectively align with the first opening in the first broach or align with the second opening in the second broach.

In some embodiments, the system can further comprise a coupling member that is configured to be selectively inserted through the channel and into the first opening so as to couple the trial neck and the first broach together, or inserted through the channel and into the second opening so as to couple the trial neck and the second broach together.

In some embodiments, the body portion of the trial neck can further comprise an anchor member. The proximal end of the first broach can further comprise a first lock member, and the proximal end of the second broach can further comprise a second lock member. The anchor member can be configured to mate selectively, engaging with the first lock member so as to resist rotational movement of the trial neck relative to the first broach, or engage with the second lock member so as to resist rotational movement of the trial neck relative to the second broach.

In some embodiments, the anchor member can be a lug extending distally from the body portion of the trial neck, and the first lock member and the second lock member can be slots on the proximal end of respective broaches. The lug can be sized and shaped so as to achieve an interference fit to the first, second or third lock members.

In some embodiments, the medial end of the neck portion can comprise a threaded segment, which is configured to insert into a threaded channel in a trial head.

In some embodiments, the system can further comprise a plurality of washers of varying thickness. Each washer can be configured to be inserted into the threaded opening of the trial head, thereby further coupling the trial head to the threaded segment can be limited by the washer so that a lateral offset of the trial head relative to the body portion of the trial neck can be at least partially determined by the thickness of the washer.

In some embodiments, the system can further comprise a third broach having a proximal end and a distal end. The proximal end of the third broach can comprise a third base. A radial cross-sectional area of the third broach can progressively increase from the distal portion of the third broach to the third base which has a third maximum area, and the third maximum area can be larger than the second maximum area. The third broach can define a third longitudinal length measured between the proximal and distal ends of the third broach, and the third longitudinal length can be larger than the second longitudinal length. The body portion of the trial neck can be releasably coupled to the proximal end of the third broach so as to define a third offset between the medial end of the neck portion and a longitudinal axis of the third broach. The second offset can be smaller than the third offset.

In some embodiments, each of the first broach and the second broach can comprise a non-metal frame member and a plurality of metal panels circumferentially coupled to the frame member. Each panel can comprise a plurality of cutting teeth. Each tooth can comprise a cutting hole on the panel and a cutting edge projecting radially outwardly from the cutting hole. The cutting edges of the plurality of cutting teeth can be spaced apart from one another along the panel.

In some embodiments, the plurality of cutting teeth on each panel can be arranged in one or more cutting zones. The cutting edges in each cutting zone can have generally same orientation angles relative to their respective cutting holes. The cutting edges in two adjacent cutting zones can differ in orientation angles relative to their respective cutting holes.

In some embodiments, the frame member can comprise a plurality of grooves adjacent to the plurality of cutting teeth of the plurality of panels so as to provide pathways for bone debris to flow through inwardly when the plurality of cutting teeth are urged against and cut a bone tissue.

In some embodiments, the frame member can comprise essentially of a biodegradable plastic material.

In some embodiments, the trial neck can comprise essentially of a plastic material.

In some embodiments, the system can further comprise a driving member. The driving member can comprise an elongated rod and an anvil top coupled to one end of the rod. The rod can comprise a threaded distal end opposite the anvil top.

In some embodiments, the rod can have a sufficiently small cross-sectional dimension so as to be selectively inserted through the first opening and into the first longitudinal lumen of the first broach, or inserted through the second opening and into the second longitudinal lumen of the second broach. A distal end of the first longitudinal lumen and a distal end of the second longitudinal lumen each can comprise a respective receiving member with threads configured to couple to the threaded distal end of the rod.

In some embodiments, the system can further comprise a handle having a distal section and a proximal section. A longitudinal axis of the proximal section can have a lateral offset from a longitudinal axis of the distal section. The distal section can be configured to selectively couple to the proximal end of the first broach or the proximal end of the second broach.

In some embodiments, the proximal section of the handle can comprise an integrated anvil top.

In some embodiments, the system can further comprise an impact member having an anvil top and a stem extending from the anvil top. The stem of the impact member can be configured to removably couple to the proximal section of the handle.

In some embodiments, the distal section of the handle can comprise a distal neck that can be selectively inserted into the first opening so as to releasably couple the handle to the first broach, or inserted into the second opening so as to releasably couple the handle to the second broach.

In some embodiments, the system can further comprise a handle coupler. The distal section of the handle can comprise a passage. The handle coupler can be selectively inserted through the passage and into the first opening so as to releasably couple the handle to the first broach, or inserted through the passage and into the second opening so as to releasably couple the handle to the second broach.

Also disclosed herein is a method of preparing prosthetic hip implantation. The method can include the acts of performing an osteotomy of a femoral neck, preparing a femoral canal, sizing the femoral canal using one or more broaches until a selected broach press fits in the femoral canal, coupling a trial neck to the selected broach, attaching a trial head to the trial neck, performing a trial reduction, and adjusting a lateral offset of the trial head relative to the trial neck if the trial reduction does not satisfy a set of predefined criteria.

In some embodiments, the act of performing the osteotomy can include activating an osteotome to remove a portion of a greater trochanter from a femur.

In some embodiments, the act of preparing a femoral canal can include creating a space inside the osteotomized femur using a first broach.

In some embodiments, the act of creating the space can include coupling a driving member to the first broach and impacting on an anvil top of the driving member with an impact force.

In some embodiments, the act of sizing the femoral canal can include comparing size of the created space to size of the selected broach and, if the size of the created space is smaller than the size of the selected broach, using one or more additional broaches of larger size to progressively enlarge the created space until the selected broach can press fit the created space.

In some embodiments, the act of coupling the trial neck to the selected broach can include aligning a channel on a body portion of the trial neck with an opening on a proximal end of the selected broach, and inserting a coupling member through the channel and into the opening. The coupling member can be configured to releasably couple the trial neck and the selected broach together.

In some embodiments, the act of attaching the trial head to the trial neck can include coupling a threaded opening of the trial head to a threaded neck portion of the trial neck.

In some embodiments, the act of attaching the trial head to the trial neck can further include inserting a washer into the threaded opening of the trial head before coupling the threaded opening of the trial head to the threaded neck portion of the trial neck.

In some embodiments, the act of performing the trial reduction can include assessing one or more performance metrics against the set of predefined criteria. The performance metrics can include leg length, leg offset, leg stability and leg tension.

In some embodiments, the act of adjusting the lateral offset of the trial head relative to the trial neck can include removing the trial head from a neck portion of the trial neck, changing washers in a threaded opening of the trial head, and reattaching the trial head to the neck portion of the trial neck.

In some embodiments, the method can further include repeating the act of performing the trial reduction and the act of adjusting the lateral offset of the trial head relative to the trial neck until the trial reduction satisfies the set of predefined criteria.

In some embodiments, the method can further include removing the selected broach, together with the coupled trial neck and the trial head, from the femoral canal.

Also disclosed herein is an assembly for preparing prosthetic hip implantation. The assembly can comprise a broach, a trial neck, a trial head, and a plurality of washers. The broach can have a proximal end and a distal end. The trial neck can have a body portion and a neck portion extending laterally from the body portion. The body portion of the trial neck can be configured to releasably couple to the proximal end of the broach. A medial end of the neck portion can comprise a threaded segment, which is configured to matingly couple to a complimentarily threaded opening on the trial head. Each washer can be configured to be inserted into the threaded opening of the trial head, thereby further coupling the trial head to the threaded segment can be limited by the washer so that a lateral offset of the trial head relative to the body portion of the trial neck can be at least partially determined by the thickness of the washer.

In some embodiments, the proximal end of the broach can comprise a base. A radial cross-sectional area of the broach can progressively increase from the distal end of the first broach to the first base which has a maximum area. The proximal end of the broach can further comprise a platform extending proximally relative to the base.

The foregoing and other objects, features, and advantages of the invention will become more apparent from the following detailed description, which proceeds with reference to the accompanying figures.

BRIEF DESCRIPTION OF THE DRAWINGS

FIG. 7A illustrates an acetabulum undersized to a reamer. FIG. 7B illustrates a schematic view of cutting teeth zones. FIG. 7C illustrates a primarily side cutting reaming action. FIG. 7D illustrates a transition from side cutting to end cutting. FIG. 7E illustrate a primarily end cutting action.

FIG. 8A illustrates a schematic view of cutting teeth zones and their general functions.

FIG. 8B illustrates the cutting teeth of the equatorial zone. FIG. 8C illustrates the cutting teeth of the transitional zone. FIG. 8D illustrates the cutting teeth of the polar zone.

FIG. 10A illustrates frictional forces associated with bone chips created by a cutting tool with a first thickness. FIG. 10B illustrates frictional forces associated with bone chips created by a cutting tool with a second thickness.

FIG. 11A illustrates stamping a flat sheet forming panels with multiple teeth designs.

FIG. 11B illustrates punching holes in the sheet. FIG. 11C illustrates stamping tooth height and forming a panel curvature.

FIG. 12 illustrates a formed dome of a reamer.

FIG. 13 illustrates a formed center support of a reamer.

FIG. 14 illustrates a form base of a reamer.

FIG. 15A illustrates an assembly of panels of a reamer. FIG. 15B illustrates an assembled reamer.

FIG. 16A illustrates stamped cutting panels of a spherical reamer. FIG. 16B illustrates an injection molding tool for creating plastic framing. FIG. 16C illustrates a finished reamer.

FIG. 17A illustrates a cylindrical reamer stamped panel. FIG. 17B illustrates a molded plastic frame. FIG. 17C illustrates another stamped panel. FIG. 17D illustrates a finished reamer.

FIG. 21 shows a side prospective view of three broaches, according to one embodiment.

FIG. 22A shows a frame member and a panel of a broach, according to one embodiment.

FIG. 22B shows a cross-sectional view of a broach, according to one embodiment.

FIG. 25A illustrates a trial neck, according to one embodiment.

FIG. 25B illustrates coupling the trial neck of FIG. 25A to a broach, according to one embodiment.

FIG. 26A illustrates a trial head and a plurality of washers, according to one embodiment.

FIG. 26B illustrates coupling the trial head of FIG. 26A to the trial neck, according to one embodiment.

FIG. 27A shows the side elevation view of a handle, according to one embodiment.

FIG. 27B shows the side elevation view of a handle, according to another embodiment.

FIG. 27C shows the side elevation view of a handle, according to a further embodiment.

DETAILED DESCRIPTION

A. General Considerations

Figure 1:
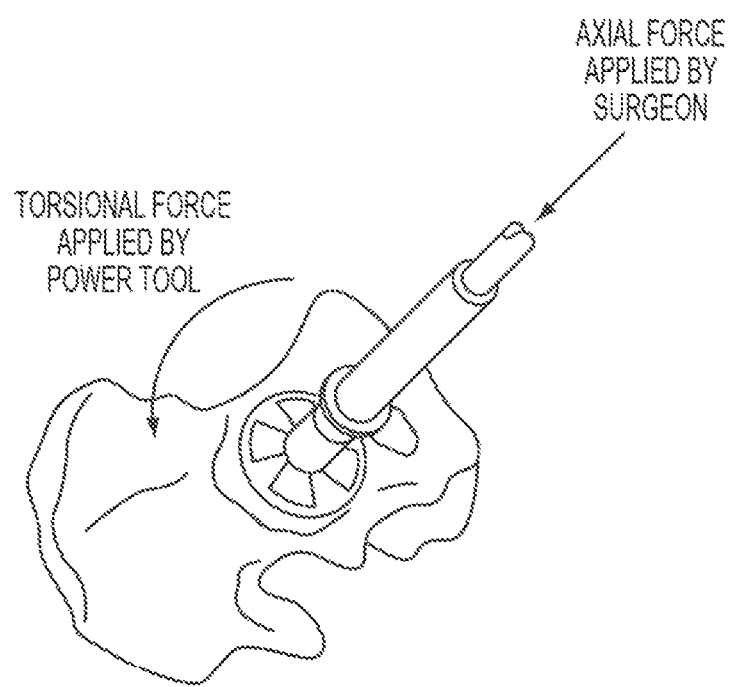
FIG. 1 illustrates an acetabular reamer, the use of the reamer to prepare the acetabulum, and a press-fit acetabular implant positioned as part of a total hip procedure.

The following description is exemplary in nature and is not intended to limit the scope, applicability, or configuration of the invention in any way. Various changes to the described embodiments may be made in the function and arrangement of the elements described herein without departing from the scope of the invention.

Although the operations of some of the disclosed embodiments are described in a particular, sequential order for convenient presentation, it should be understood that this manner of description encompasses rearrangement, unless a particular ordering is required by specific language set forth herein. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art when viewed in light of this disclosure.

It should be understood that the disclosed embodiments can be adapted to prepare orthopedic surgery other than hip implantation. For example, the disclosed systems and methods can be adapted for preparation of prosthetic shoulder implantation or other surgical procedures.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

As used herein, the term "approximately" and "about" means the listed value and any value that is within 10% of the listed value. For example, "about 10 mm" means any value between 9-11 mm, inclusive.

As used in this application and in the claims, the terms "a," "an," and "the" include both the singular and plural forms of the element(s) they refer to unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

As used herein, the term "effective functional life" means the amount of use a tool can experience before it begins to operate sub-optimally for its intended purpose. In some embodiments, the effective functional life can be based on a number of uses of the tool and/or an amount of time the tool has been used. As used herein, the term "powered driving member" means any device capable of driving a cutting tool such as, for example, a drill.

As used herein, the term "single-use" tool or instrument means a tool or instrument that is configured and/or intended to be used once before being discarded. Thus, a single-use tool or instrument can be a non-reusable device in contrast to reusable tools or instruments which, subject to certain procedures such as cleaning and sterilization, may be used more than once. As used herein, the term "disposable" device or instrument means a device or instrument that is configured and/or intended to be used one or a few times before being discarded.

Directions and other relative references (e.g., inner, outer, etc.) may be used to facilitate discussion of the drawings and principles herein, but are not intended to be limiting. For example, certain terms may be used such as "inside," "outside,", "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. As used herein, "and/or" means "and" or "or", as well as "and" and "or".

B. Cutting Tools

It is generally desirable that cutting surfaces on a cutting tool (e.g., cutting teeth) be as accurate and consistent as possible for the dimensional accuracy of the final preparation in the bone. For example, cementless acetabular implants (press fit) are dependent on their dimension and the dimension of the bone preparation to create a reproducible interference fit for establishing initial stability of the implant. FIG. 1 illustrates an acetabular reamer, the use of the reamer to prepare the acetabulum, and a press-fit acetabular implant positioned as part of a total hip procedure.

The initial stability of the implant is critical to long term success and if the implant moves large amounts (e.g., 75 microns or more) under physiological loads post-operatively, it can result in soft tissue growing into the implant rather than bone. If this occurs, the implant will eventually loosen. Accordingly, the accuracy of the initial fit must provide stability of the implant to allow bone to grow into the implant during the first 6-12 weeks after surgery. In some instances, the interference level required for cementless acetabular implants can be required to be very small (e.g., less than 2 mm, and, in some cases, preferably less than 1 mm). However, commercial cutters can vary in their accuracy by as much as 0.25 mm and these variations can result in initial acetabular implant stability. Because the initial interference fit provides stability to the implant, improved accuracy of the teeth height and performance can assist in achieving this goal.

Configuration of Cutting Members

Conventional reamer designs use the same cutting tooth geometry within each design. These teeth are also positioned at 90° to the latitude lines of the spherical reamer surface.

However, cutting teeth around the equator of the reamer perform a side cutting function while teeth towards the dome of the cutter perform an end cutting function.

As described in more detail herein, various embodiments are provided in which reamers utilize different cutting teeth configurations and different orientations to address the different bone cutting requirements and thereby improving the efficiency of the cut. By efficiently designing cutting teeth for specific operations, faster bone cuts can be achieved, thereby producing less friction. Minimizing the friction generated by the reamers relates directly to maintaining the life of the bone. Friction can lead to heat and if the cutter-bone interface reaches temperatures above 50° C. (122° F.) bone death (necrosis) can occur. This can affect long term success of the procedure whether the implant is used with or without bone cement. If the bone preparation bed is damaged due to excessive heat generated from the acetabular cutter, the fixation of the implant will be compromised and can lead to loosening and revision.

Figure 2C:
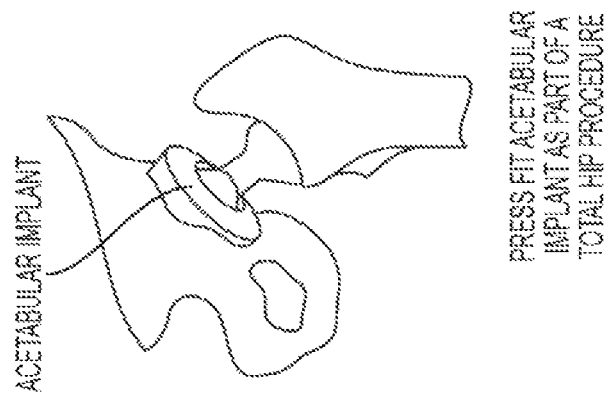
FIG. 2C illustrates the acetabular implant in position as part of a total hip procedure.
Figure 2B:
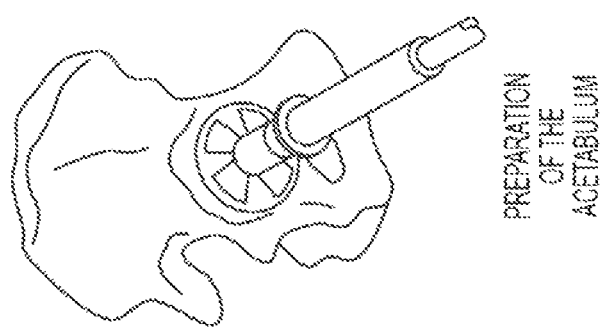
FIG. 2B illustrates axial force applied by a surgeon, by pushing the cutter into the acetabulum and a second torsional force exerted by the power reaming tool.
Figure 2A:
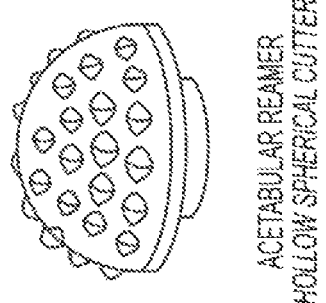
FIG. 2A illustrates an acetabular reamer with a hollow spherical cutter.

There are two primary forces applied to the reamer during the machining of the bone. When considering an acetabular reamer, as shown in FIG. 2, there is an axial force applied by the surgeon who pushes the cutter into the acetabulum and a second torsional force exerted by the power reaming tool. In some embodiments, the novel cutting tools disclosed herein convert the torsional force into a force applied at the cutting tooth edge to improve the efficiency of the cut.

The systems and methods described herein for forming cutting tools can provide greater control and accuracy of the tooth sharpness, cutting angles, and resulting bone chip removal by the tool. In addition, as described in more detail below, the cutting tools described herein can be formed by novel manufacturing processes that permit the creation of multiple teeth in one operation.

Figure 3B:
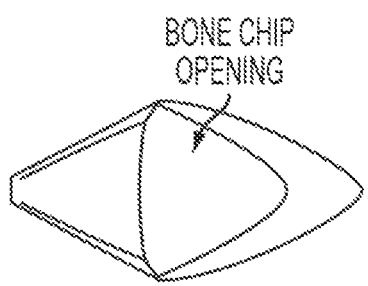
FIG. 3B illustrates a bone chip opening.
Figure 3C:
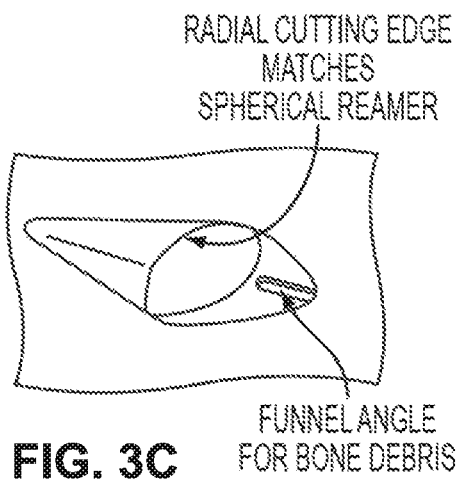
FIG. 3C illustrates a funnel angle for bone debris.
Figure 3A:
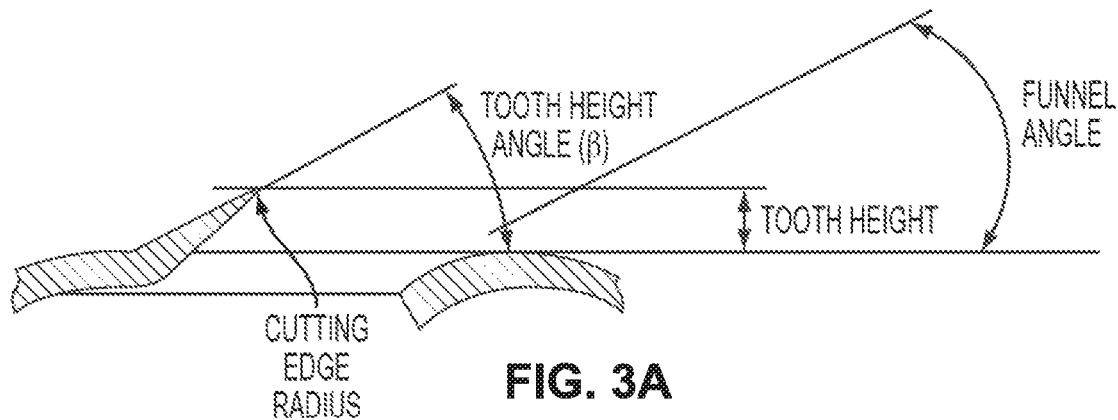
FIG. 3A illustrates a cutting tool composed of a sharp tooth edge, a specific tooth elevation, specific cutting angle, a specific tooth orientation to the axis of rotation and a peripheral opening around the cutting edge providing an improved flow path for the bone debris.
Figure 4A:
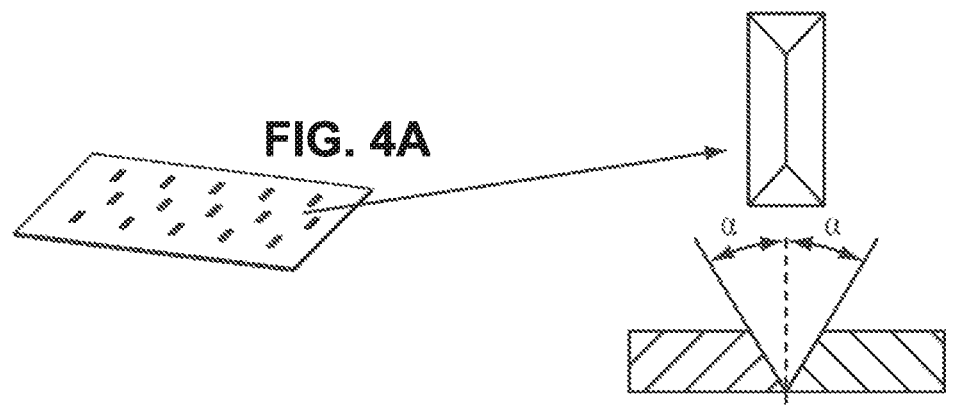
FIG. 4A illustrates a manufacture of cutting teeth geometry by forming a sheet.
Figure 4B:
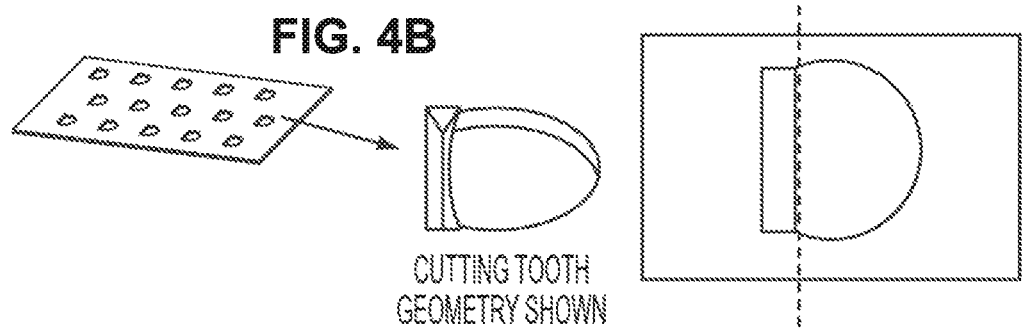
FIG. 4B illustrates cutting tooth geometry of the sheet.
Figure 4C:
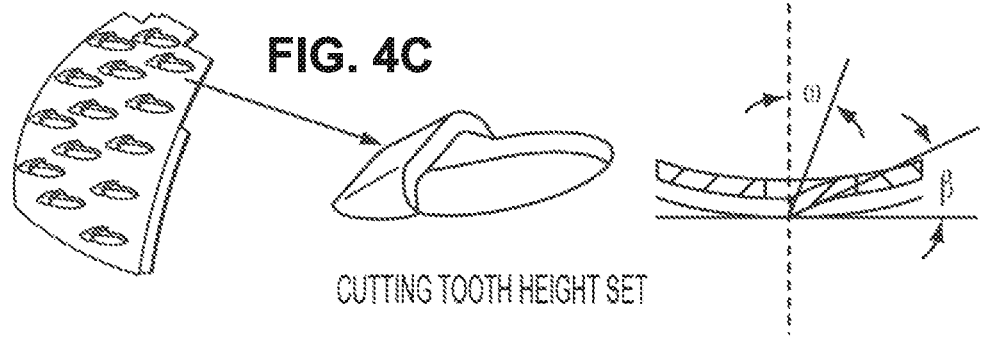
FIG. 4C illustrates a cutting tooth height set.

In the embodiments described herein, cutting surfaces (e.g., teeth) can comprise a sharp tooth edge (tolerance 0.0005" to 0.002" tooth edge radius), a specific tooth elevation (tolerance 0.002"-0.004"), specific cutting angle, a specific tooth orientation to the axis of rotation (e.g., tool angle), and a peripheral opening around the cutting edge providing a designed flow path for the bone debris as shown in FIG. 3. This tooth geometry can also be manufactured according to FIG. 4 through a series of stamping operations allowing for multiple teeth to be made at the same time. For example, as illustrated in FIG. 4, a flat sheet of material (e.g., metal) can be stamped so that a plurality of "V"-type cavities are punched into the sheet based on a desired cutting angle ω. Next, a plurality of holes can be punched around the "V"-type cavities (or grooves), creating a cutting edge. If necessary, another stamping step can be performed to stamp the tooth height and curvature in operation (or multiple operations if desired). As shown in FIG. 4, angle β determines the tooth height and angle β in conjunction with angle α will determine the rake angle ω (ω=α−β) of the cutting surface. In some embodiments, the rake angle can vary between about 5 and 25 degrees, and in other embodiments between about 5 and 15 degrees (e.g., about 10 degrees)

Thus, in contrast to conventional devices, the tooth angle (α) can be established in the first forming operation and can be set (ω and β angles) based on the intended function. Multiple iterations of this tooth design can be provided in specific zones of the reamer surface which address the intended type of cutting required at those locations.

Figures 5A, 5B:
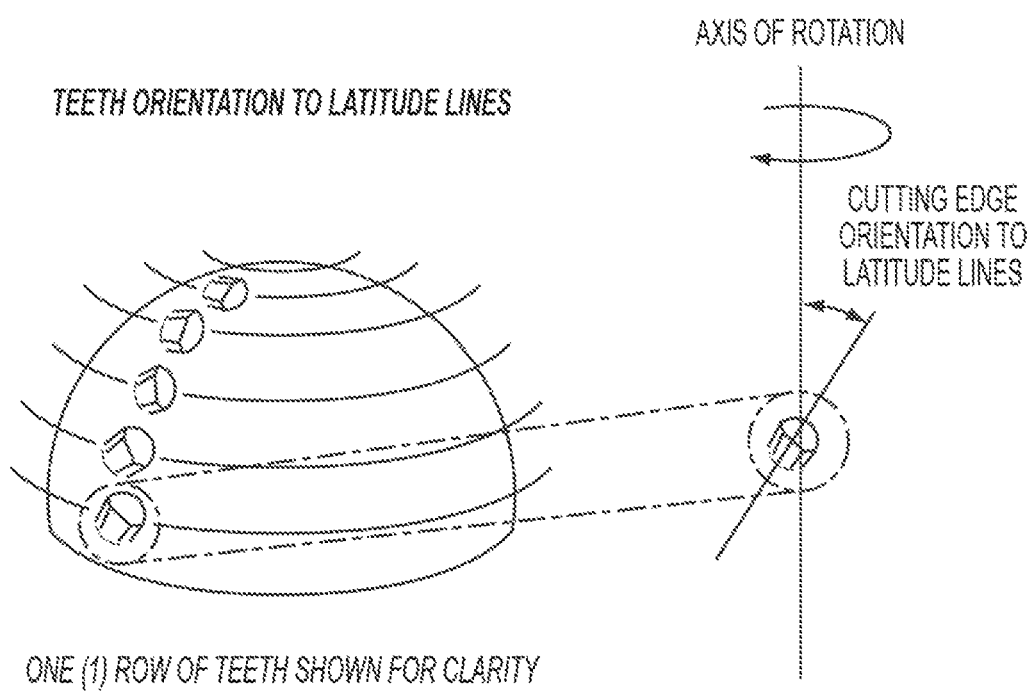
FIG. 5A illustrates a novel cutting tool having a plurality of teeth, with one row of teeth shown for clarity.
FIG. 5B illustrates the cutting edge orientation to latitude lines.
Figure 6:
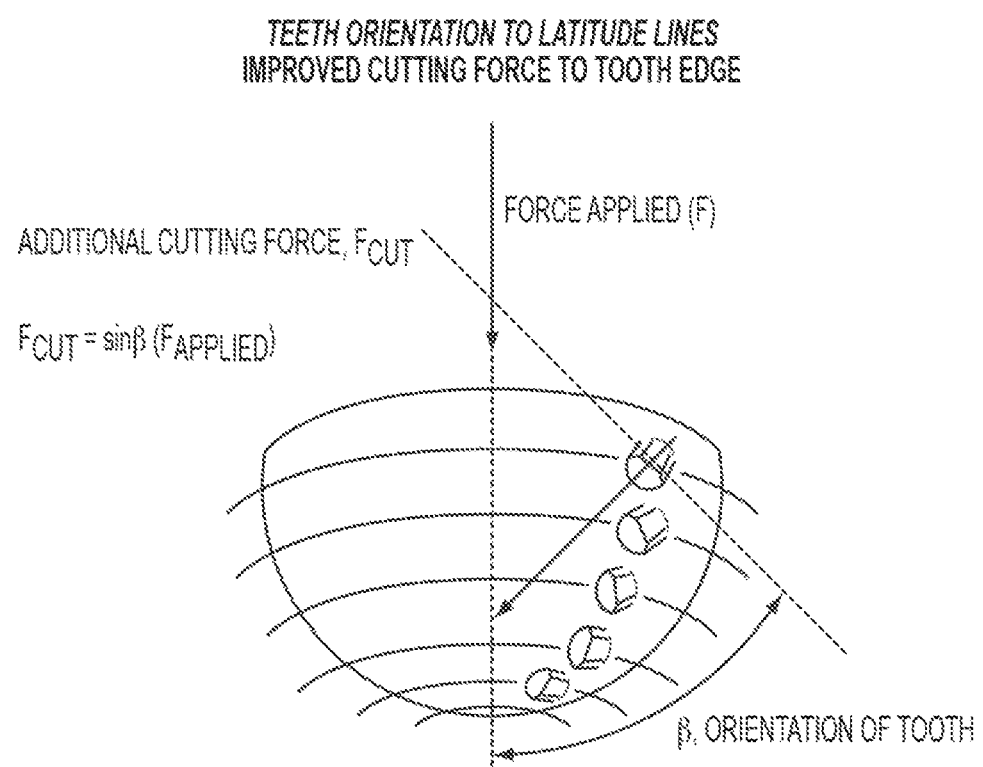
FIG. 6 illustrates a novel cutting tool having a plurality of teeth.

In some embodiments, the novel cutting tools disclosed herein can have teeth arranged in a spiral or helix manner on the surface of the cutter. However, the tooth designs and tooth orientations can be optimized to reduce the reaming time required to complete the preparation. As shown in FIGS. 5-8, the cutting edges of the teeth can be oriented at different angles to the lines of latitude based on the required cutting functions at various positions on the surface of the reamer. This can provide for a faster cut by converting the rotational energy into linear energy assisting in advancing the reamer into the preparation analogous to a screw thread (FIG. 5). The tooth orientation can further improve the cutting force at the tooth edge. By changing the orientation of the cutting edge relative to the latitude lines, a portion of the torsional force is converted into a cutting force at the tooth edge as shown in FIG. 6. This improvement primarily benefits the teeth closest to the equator as they are performing a side cutting function.

As shown in FIGS. 5-6, the angle of orientation of the cutting edge relative to axis of rotation can increase from the equatorial teeth to the polar teeth and decrease relative to the latitude lines. At least three different types of cutting teeth (e.g., orientation angles and/or cutting angles varying) can be provided on the tool. In some embodiments, at least three regions are provided with similar type teeth in each region. In other embodiments, the teeth can vary in a transitional manner effectively providing more than three zones.

In some embodiments, relative to the latitude lines, the range of variation can be orientation angles of between 10 and 30 degrees (more preferably between 15 and 25 degrees—e.g., 20 degrees) for the equatorial zone, orientation angles of less than 5 degrees (more preferably about 0 degrees) in the polar zone, and somewhere in between for the orientation angles in the transition zone (e.g., between 0 and 20 degrees, or preferably between 5 and 15 degrees— e.g., 10 degrees). A benefit of the larger orientation angles in the equatorial zone is a portion of the axial load applied by the operator will be converted into driving the cutting edge into the bone. As you move to the polar zone, the angle of the tooth on the surface has less effect as the tooth becomes perpendicular to the direction of the cut. That is, the specific tooth geometry in the polar zone needs to address an end cutting ability rather than a side cutting ability.

FIG. 7 illustrates an exemplary process by which a cutting tool (e.g., a spherical reamer) transitions from engagement with the bone at one area to another area of the cutting tool. As used herein, the term "polar teeth" refer to cutting surfaces at and/or adjacent the pole of the spherical reamer, the term "equatorial teeth" refer to cutting surfaces at and/or adjacent to the equator of reamers having a hemispherical shape (e.g., the area furthest from the poles in FIG. 7), and the term "transition teeth" refer to cutting surfaces between the polar and equatorial teeth.

In the exemplary reaming process illustrated in FIG. 7, the spherical reamer begins by introduction into the concave surface of the acetabulum. It is noted that this initiation of the cut involves just the equatorial teeth. These equatorial teeth are performing more of a side cutting function and therefore can have a specific tooth angle based on this intended function. Additional teeth (i.e., the transitional teeth) become engaged with the bone as the reamer is further introduced into the acetabulum. The transitional teeth perform a combination of side-cutting and end-cutting and can be optimized for this purpose. As the reamer becomes fully inserted into the preparation site, the teeth at the pole (i.e., the polar teeth) of the reamer serve to primarily end-cut.

Thus, the teeth can have different cutting demands depending on their location on the surface of the reamer and can be configured accordingly. FIG. 8 illustrates the manner in which the cutting angles of the teeth can vary in accordance with the required cutting function of the bone. The table below illustrates the types of teeth and their configurations as reflected in FIG. 8.

| Teeth Region | Cutting angle (defined relative to a side surface of the cutting tool) | Tooth edge radius | Funnel angle | Tooth height |
| --- | --- | --- | --- | --- |
| Equatorial | 15-35 degrees (more preferably, 20-30 degrees) | 0.0005-0.002" | 20-40 degrees, (more preferably, 25-35 degrees) | 0.020 ± 0.002" |
| Transition | 35-55 degrees (more preferably, 40-50 degrees) | 0.0005-0.002" | 20-40 degrees, (more preferably, 25-35 degrees) | 0.020 ± 0.002" |
| Polar | 55-75 degrees (more preferably, 60-70 degrees) | 0.0005-0.002" | 20-40 degrees, (more preferably, 25-35 degrees) | 0.020 ± 0.002" |

In certain embodiments, the teeth in each of the three zones can generally have the same characteristics, whereas the teeth in two adjacent zones can have different characteristics. For example, the teeth in each zone can have the same cutting angle, whereas the teeth in two adjacent zones can have different cutting angles. In one exemplary embodiment, the teeth in the equatorial zone can have the same first cutting angle (e.g., 25 degrees), the teeth in the transition zone can have the same second cutting angle (e.g., 45 degrees), and the teeth in the polar zone can have the same third cutting angle (e.g., 65 degrees). Similarly, the teeth in each of the three zones can generally have the same tooth edge radius, funnel angle, or tooth height, whereas the teeth in two adjacent zones can have different tooth edge radius, funnel angle, or tooth height.

In alternative embodiments, the teeth in each of the three zones can vary in characteristics (cutting angles, tooth edge radius, funnel angle, tooth height, etc.). For example, the cutting surfaces can transition gradually from one zone to another. Thus, polar teeth can transition gradually from polar teeth with the orientation and characteristics noted above to transition teeth with the orientation and characteristics noted above. In this manner, for example, some teeth can have orientation and characteristics of polar teeth (e.g., 65 degree cutting angle), some can have characteristics of transition teeth (e.g., 45 degree cutting angle), and some teeth between the polar teeth and transition teeth can have characteristics somewhere inbetween (e.g., 55 degree cutting angle). In one example, the cutting angle in the polar zone may gradually decrease from about 70 degrees at the pole region to about 60 degrees at the polar-transition zone boundary; the cutting angle in the transition zone may gradually decrease from about 50 degrees at the polar-transition zone boundary to about 40 degrees at the transition-equatorial zone boundary; and the cutting angle in the equatorial zone can gradually decrease from about 30 degrees at the transition-equatorial zone boundary to about 20 degrees at the equatorial region.

Proper bone chip exit paths can also contribute to an improved surgical preparation. With a non-impeded path for the bone chips to travel away from the cutter, it enables the instrument to produce a faster and cooler bone cut. As shown in FIG. 3, openings can be provided adjacent cutting surfaces to provide a "funnel" that permits bone chips to efficiently flow from the face of the reamer to avoid additional torque requirements to drive the cutter. Without such openings, increased torque is required to drive the cutting tool and such increased torque is usually accompanied by increased axial pressure as the operator senses the resistance in advancing the cutter and applies increased loads. This combination generates increased heat through friction capable of generating temperatures which can cause bone necrosis.

Manufacturing of Cutting Tools

Figure 9:
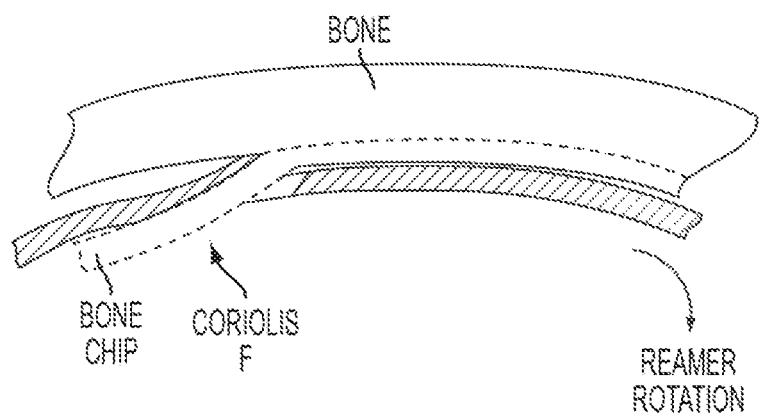
FIG. 9 illustrates a schematic view of cutting forces applied by a cutting tool.

In some embodiments, the novel cutting tools can be manufactured by forming the spherical body and teeth from thinner sheet metal, 0.005"-0.020", which can improve the efficiency in manufacturing (longer tool life of the forming tools) and ability to create a sharp tooth edge without a specific sharpening operation. In addition the thinner material better dissipates the heat generated from the friction of cutting the bone over a thicker walled, heavier mass reamer. The thinner material also produces less friction, therefore a lower temperature at the surface, through reduction of the Coriolis forces (FIG. 9).

FIG. 10 illustrates a comparison of the frictional forces associated with bone chips created by cutting tools having different thicknesses. As shown in FIG. 10, for thicker walled cutters (e.g., cutters with wall thicknesses greater than 0.022"), the bone chip particles must travel a greater distance in contact with the cutting surface of the cutter. As a result, lower temperatures can be achieved by producing cutters with wall thickness of between 0.005" and 0.020". The following novel manufacturing methods can be used to produce cutting tools with such reduced wall thicknesses.

FIG. 11 illustrates exemplary operations for manufacturing cutting tools. As shown in FIG. 11, panels can be formed with multiple teeth designs and a reamer can be assembled as shown. This design and method of manufacturing a spherical reamer can be faster and more efficient than conventional techniques. In some embodiments, this method can be produced in fewer steps, such as in nine operations. In comparison, some conventional approaches of manufacturing of cutting tools can require hundreds of operations to form a spherical reamer.

As shown in FIGS. 11A-11C, 12-14, and 15A and 15B, stamped cutting panels can be formed by punching cavities in a flat sheet, forming holes for receiving bone chips, and setting panel curvature and teeth height. A center support, base, and dome can be formed and assembled with the panels to form a single cutting tool. Thus, for example, in some embodiments, the following steps can be taken:

1. The specific tooth cutting angle is punched into a flat metal blank with accuracy of 0.001±0.0005" as the first step. Angle can be set based on intended cutting requirements of the bone.
2. Punch opening for bone chips around tooth and create cutting edge.
3. Form spherical section from the flat metal blank and elevate all teeth above spherical surface with tooth elevation tolerance of ±0.002". Teeth are formed as contours of the intended spherical surfaces as opposed to just straight edges. The opening around the teeth can be further formed into funnels at specific angles to direct the bone chips away from the outer surface and into the hollow cavity of the cutter.

4. Multiple panels are formed (3 to 8 for example) which are assembled and laser welded together forming a spherical reamer.

Using the manufacturing techniques described herein, any number of teeth (e.g., 1-20 or more) can be made in a single forming step. In contrast, conventional systems require multiple forming steps for each individual tooth. Because the number of operations required to manufacture a spherical reamer can be greatly reduced, the costs are similarly reduced, thereby providing a lower cost, yet equally effective, cutting tool that can be removed from clinical service at a the end of its functional life without significant financial loss.

It should be understood that the supporting structure for the panels can be formed in various manners. For example, FIGS. 16A-16C illustrate an alternative approach in which the panels are secured by a plastic molded part.

In some embodiments, the panels are placed directly into an injection molding tool and a medical grade plastic (e.g., PEI (polyetherimide, ULTEM®), PEEK (polyetheretherketone), PAI (polyamidide, TORLON®) can be injected around the periphery of the panels creating a frame that encloses and secures the panels. FIGS. 17A-17D illustrate a similar structure to that illustrated in FIG. 16C; however, instead of a spherical reamer, FIG. 17D depicts a cylindrical reamer.

The cutting tools can be color coded to facilitate identification of the various sizes and types of cutting tools. When the cutting tool frames are formed by injection molding, such color coding can be achieved by varying the color of the injection molded plastic part.

Laboratory testing of a disclosed embodiment provided a comparison to existing art spherical reamers. Bovine bone specimens were used to monitor the speed to prepare a standard preparation, the temperature generated during that preparation and how many preparations could be completed before cutting edge damage generated a temperature exposure to the bone above 50° C. (122° F.). FIG. 12 summarizes the results of this testing and illustrates some of the improvements, such as the ability to cut bone at a lower temperature for a greater number of uses.

All cutting tools will eventually wear at the cutting edges resulting in a non-efficient cutter which would need to be sharpened or discarded. This is true of all industries including the medical field where these cutters are machining bone. In this field, the consequences of the cutter becoming dull and continuing to use it can result in bone necrosis. This in turn can jeopardize the success of the surgical procedure as the prosthesis must be supported by live, healthy bone to stabilize the implant. Excessive heat will kill the bone leading to bone resorption and a less than ideal interference fit between the bone and the implant. The rounding of the teeth cutting edges and damage to these edges can be demonstrated after 4-6 uses of these reamers in cow bone. It is for that reason all cutters should be qualified through laboratory testing to define the maximum number of uses under worst-case conditions which will not violate the temperature threshold for killing bone. This test result can then be used as a method to identify when the cutter should be removed from use.

Figure 18:
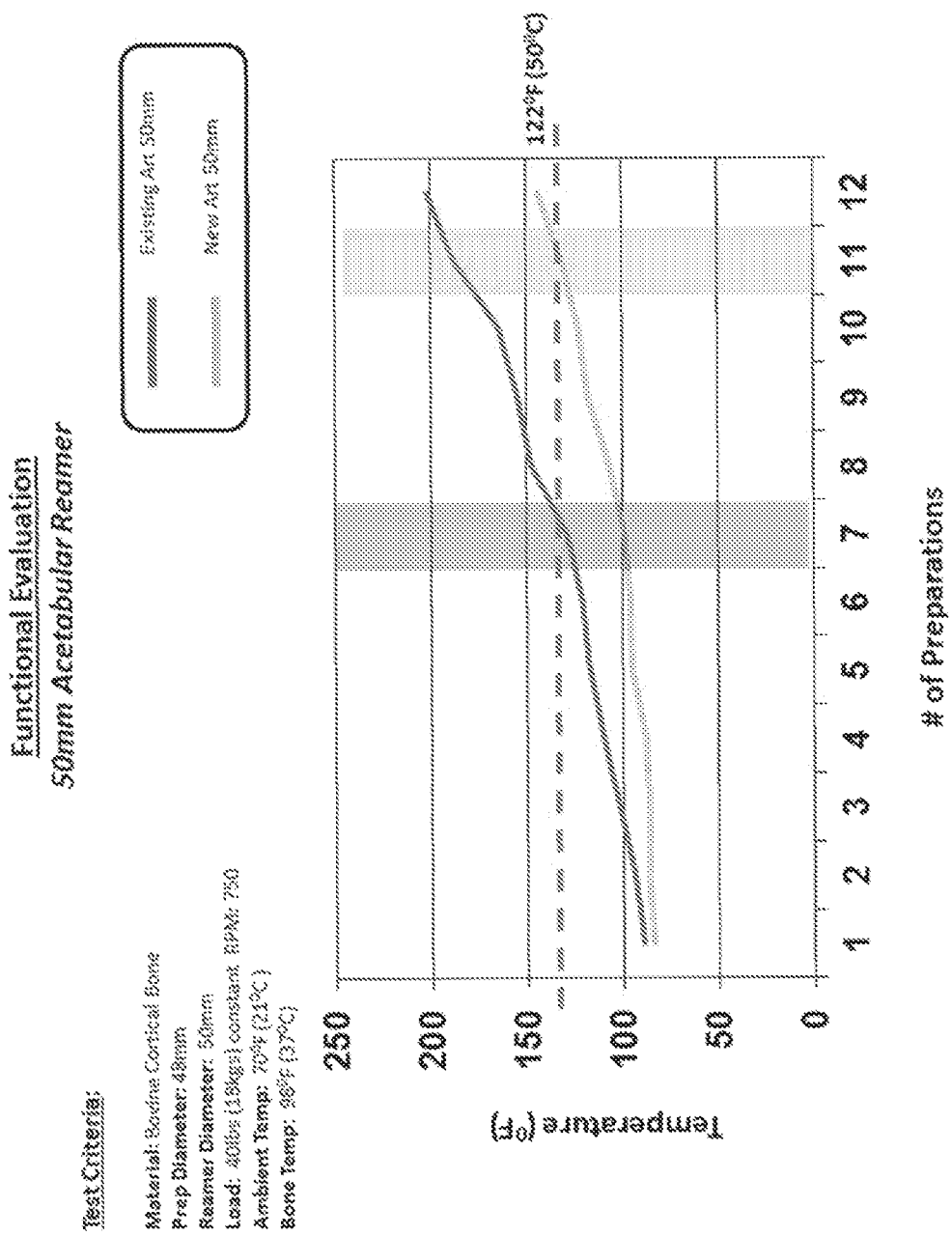
FIG. 18 illustrates the results of an exemplary test procedure.

FIG. 18 illustrates a laboratory test set-up for determining the effective functional life of a cutting tool. In these tests, acetabular reamers were used to cut bone (i.e., cortical bovine bone) to determine the number of uses the acetabular reamers can experience before the end of their effective functional life. In one example, it was determined that approximately six (6) uses of the reamer produces a complete preparation without generating excessive heat (e.g., temperatures at or above 122° F. (50° C.)).

Figure 19:
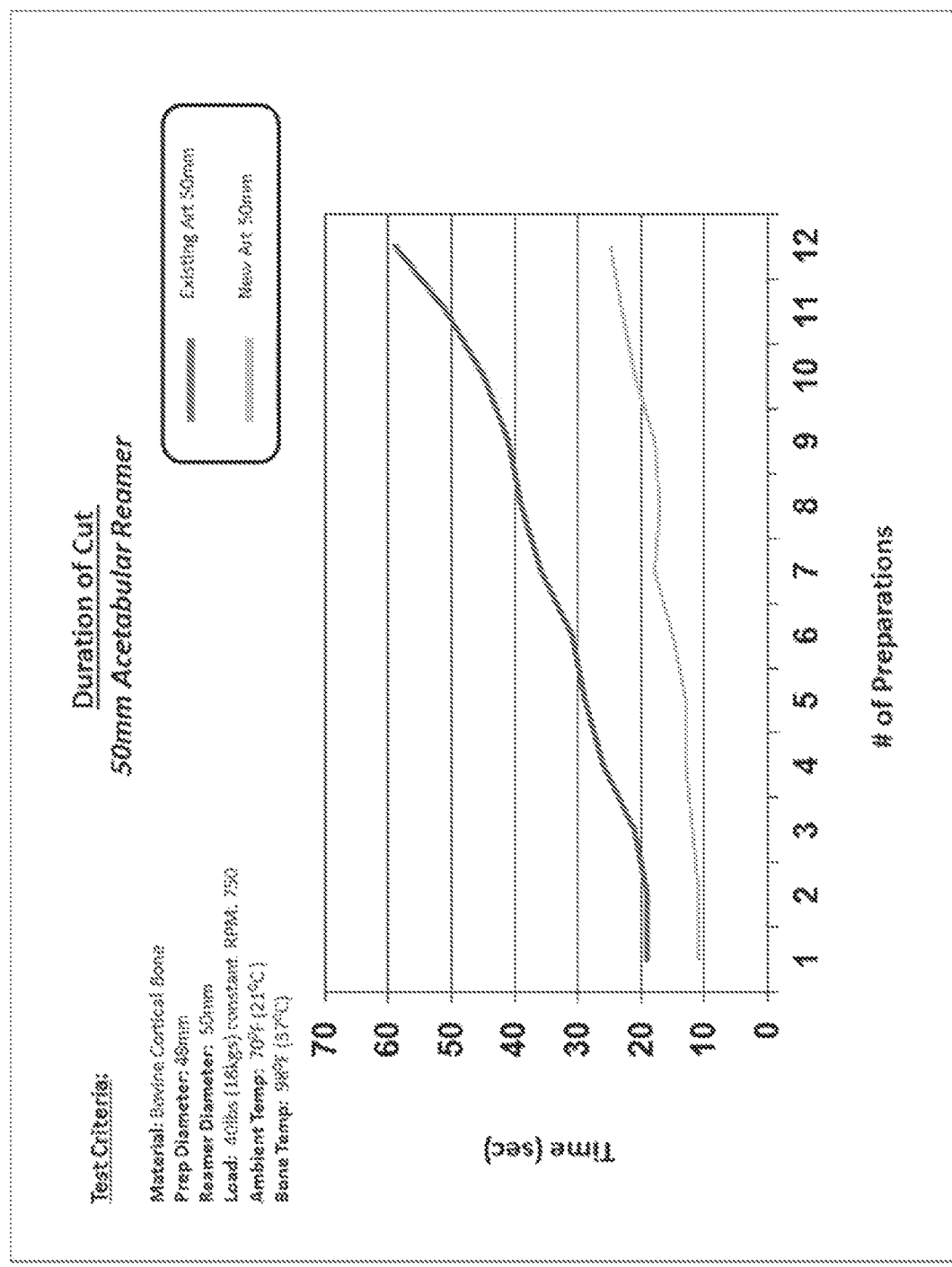
FIG. 19 illustrates the results of an exemplary test procedure.
Figure 20A:
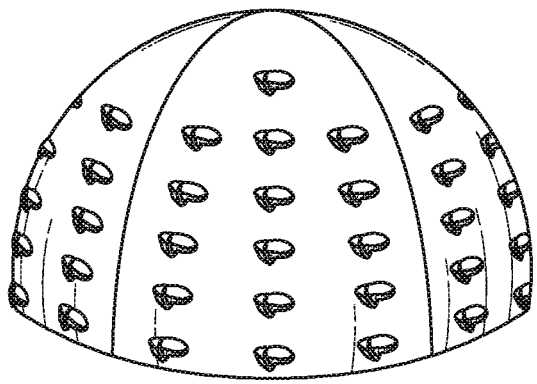
FIG. 20A illustrates an exemplary cutting tool of at least some of the disclosed embodiments, which is a spherical reamer.
Figure 20B:
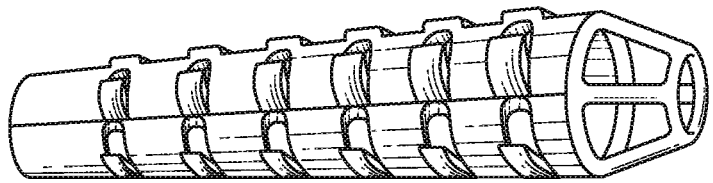
FIG. 20B illustrates an exemplary cutting tool of at least some of the disclosed embodiments, which is a long bone tapered reamer.
Figure 20C:
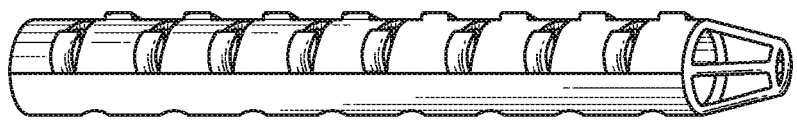
FIG. 20C illustrates an exemplary cutting tool of at least some of the disclosed embodiments, which is a cylindrical reamer.
Figure 20D:
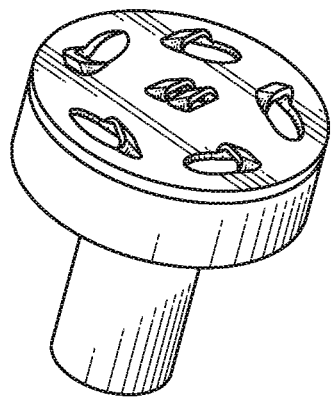
FIG. 20D illustrates an exemplary cutting tool of at least some of the disclosed embodiments, which is a patellar reamer.

FIGS. 18-19 also illustrate the results of an acetabular reamer evaluation in bovine bone, including (1) a chart showing the functional evaluation of a 50 mm acetabular reamer to cut bovine bone, graphing the number of bone preparations (i.e., uses of the cutting tool) and the temperature in the bone preparation area (FIG. 18); and (2) a chart showing the functional evaluation of a 50 mm acetabular reamer to cut bovine bone, graphing the number of bone preparations (i.e., uses of the cutting tool) and the time required to achieve the bone preparation (FIG. 19). As shown in FIG. 18, continuing to use the cutter after the sixth use consistently resulted in a longer preparation time and increased heat generation. The sharpness of the teeth cutting edges are directly proportional to the load required to advance the cutter, and therefore the resulting friction/heat generated. As the cutting edge rounds (or dulls), it becomes less effective in penetrating the surface of the bone and requires additional load to attempt to advance it. This cutter wear is generally consistent for all cutting tools.

FIGS. 20A-20D illustrate exemplary cutting tools of at least some of the disclosed embodiments, including a spherical reamer, long bone tapered reamer, cylindrical reamer, and patellar reamer. The cutting tools and methods of manufacturing the same can provide a number of improvements, including (in certain embodiments) at least some of the following improvements:

1. Multiple teeth designs and teeth orientations to address multiple machining needs of the bone yielding a faster, cooler cut.
2. Tooth design geometries which address side cutting, end cutting and a combination of both.
3. A thinner material for forming the spherical reamer which can improve sharpness and reduction of heat.
4. A thinner material which also provides for more efficient forming of teeth and component parts improving manufacturing tool life.
5. Ability to produce multiple teeth designs and multiple teeth in fewer manufacturing steps.
6. A method of assembling a spherical reamer using multiple panels, pre-stamped with teeth of specific geometry and orientation.

The novel approach to producing more efficient medical reamers described herein can help ensure a proper bone preparation for every patient. In addition, the cutting tools described herein can provide improved sharpness, reduced heat during the reaming and a faster preparation based on tooth geometry and orientation. These improvements are also possible through a less expensive manufacturing process which makes it more economical to discard the reamer when it becomes dull.

Functional Life of Cutting Tools

It is also desirable to understand the effective functional life of the cutting tools described herein. As with any cutting tool, no matter how efficient the cutter has been designed, it will dull after multiple uses and its effective life will have terminated. Currently medical spherical reamers are used multiple times without any monitoring of the status of where the cutter is in its life cycle. Hospitals receive a new spherical reamer and follow an instrument processing procedure that includes cleaning, sterilizing, use, cleaning, sterilizing, and reuse. However, that cycle can continue for many, many surgical procedures before a surgeon notices the reamer is not cutting well.

Cutting teeth dull after even a few uses and dull cutting teeth generating heat that can be sufficient to cause bone necrosis. Accordingly, in addition to improving teeth design, it can also be helpful to provide the ability to indicate when a cutter should be removed from use to avoid issues relating to bone necrosis from dull cutters. In conventional approaches, instruments are used in hospitals on patients many times without knowledge of the life expectancy of the reamer and often beyond the functional life of the instrument. Some of the reluctance to discard the instrument after a single use is the cost of manufacturing these instruments. It is also perceived by the medical industry through orthopedic surgeons that these instruments do have a functional life greater than a single use. Accordingly, significant improvements in manufacturing costs, such as those realized by the embodiments described herein, can help to reduce the number of uses needed to obtain a return on investment.

As described above, the methods described herein can create more cost effective cutting tools, such as spherical reamers. In addition, the methods described herein can provide a means for defining the effective functional life of the cutting tools and providing a method of knowing when to discard it to ensure that the cutting tool used for any procedure (e.g., a total hip procedure) will be effective for its intended purpose.

In at least some of the embodiments described herein, as described above, novel medical reamers can include at least some of the following design parameters, enabling the production of more efficient tools for cutting bone:
1. Optimize forces applied to the reamer.
2. Thin, sharp tooth edge.
3. Specific tooth designs and tooth orientations providing a faster completion of the reaming cycle.
4. Adequate bone chip exit path to minimize friction from the flow of the chips at the cutter surface.
5. Minimize friction from cutting by using thinner materials and improved tooth geometry.
6. Define the functional life of the cutting edges through laboratory testing to know when to discard the reamer.
7. Provide an improved and efficient manufacturing process.

Laboratory testing to confirm an improved speed of the preparation, a lower cutting exposure temperature to the bone and an increased functional life to the reamer.

It should also be understood that these design principles can be incorporated into other cutting tools than those described in the figures, such as medical reamers that are used for patella resurfacing, glenoid reaming and machining the canal of long bones.

C. Sterile Kit

During prosthetic hip implantation, after preparing the acetabular socket (e.g., by using the acetabular reamer described above) and performing osteotomy of the femoral neck, the femoral canal can be prepared to accommodate the femoral stem of the hip implant. Traditionally, a large set of devices are needed to prepare the femoral canal. For example, a canal finder or a tapered or hollow reamer (see, e.g., FIGS. 20B-20C) may be needed to initially open the medullary canal. Then a plurality of rasps of progressively increasing size need to be sequentially inserted into the canal, and each rasp needs to be impacted to the level of osteotomy. To perform trial reduction after the femoral canal is prepared, a plurality of trial necks with different sizes are necessary in order to adjust the lateral offset and height of the trial head that is to be connected to the trial neck.

Maintaining such a large set of surgical components is a challenging task. Not only does it increase the inventory cost, but also increase the labor cost for unpacking, sorting and checking for completeness of those components. Moreover, the rasps are particularly difficult to sterilize. Although using disposable rasps may reduce the burden of sterilization, it can be associated with significantly increased expense because conventional rasps are made of high-strength metal in order to provide desired cutting performance. Substituting metal with cheap material (e.g., plastic) in disposal rasps may reduce cost but may also compromise the cutting performance.

Also disclosed herein is a simplified sterile kit or system, which contains only the instruments necessary to perform the particular surgery. Such a simplified sterile kit would greatly facilitate the preparation of hip prostheses, avoiding expensive, time consuming and often incomplete sterilization, delays having to wait for the sterilization and the long "set up time" required for hip surgical procedures.

As disclosed herein, the system includes disposable cutting tools (e.g., broaches), which can be made of low-cost materials while providing the desired high cutting performance. The molded plastic instruments with stamped metal cutting surfaces are high performance tools which function similarly to solid metal rasps, but can be produced at a much lower cost, making disposability economically practical. Unlike multi-used rasps, the new disposable cutting tools can always remain sharp.

The instruments in the kit also allow for some flexibility, as the size of the implant required may not be exactly what is templated before surgery. In addition, the kit is simplified by including multi-functional devices, which can be used to perform multiple orthopedic procedures efficiently. Such multi-functional devices can be simple in design and made of cheaper, less durable materials, thus accommodating the ongoing shift of surgery to less comprehensively stocked and less costly ambulatory surgical centers.

Some of the instruments that can be included in the system are described more fully below.

Broaches

FIG. 21 illustrates three broaches 100, 200, 300 of different sizes (small, medium, large) that can be included in the system. Although three broaches are shown, it should be understood that the system can include any number (e.g., 1, 2, 4, 5, etc.) of broaches having similar structure but different sizes. As described below, these broaches can be used to create and size the femoral canal, as well as for trial reduction. Generally, each broach 100, 200, 300 can be shaped and sized to match a corresponding prosthetic femoral stem to be used for implantation.

Each of the broaches 100, 200, 300 can have generally the same structure and be manufactured according to the method described above. For example, FIG. 22A shows that the broach 100, taken as being representative, can comprise a non-metal frame member 110 and a plurality of metal panels 120 circumferentially coupled to the frame member 110. In some embodiments, the frame member 110 can comprise essentially of a plastic material. In some embodiments, the plastic material can be biodegradable.

Each panel 120 can comprise a plurality of cutting teeth 122. Each tooth 122 can have a cutting hole 124 on the panel 120 and a cutting edge 126 projecting radially outwardly from the cutting hole 124. The cutting edges 126 of the plurality of cutting teeth 122 are spaced apart from one another along the panel 120. The panels 120 can be formed with multiple teeth designs by using stamped punching and cutting technique, similar to the method of manufacturing spherical reamer described above. The metal panels 120 can then be assembled with the plastic frame member 110 to form a single broach 100.

In some embodiments, similar to the spherical reamer described above, the plurality of cutting teeth 122 on each panel 120 can be arranged in one or more cutting zones (e.g., 128a, 128b, 128c). The cutting edges 126 in each cutting zone can have generally same orientation angles relative to their respective cutting holes 124. The cutting edges 126 in two adjacent cutting zones can differ in orientation angles relative to their respective cutting holes 124.

In some embodiments, the frame member 110 can include a plurality of grooves 121 adjacent to the plurality of cutting teeth 122 of the plurality of panels 120 so as to provide pathways for bone debris to flow through inwardly when the plurality of cutting teeth 122 are urged against and cut a bone tissue.

Because the cutting can be done by the teeth 122 of the stamped metal panels 120, the plastic frame member 110 does not have to be sufficiently hard to not break or fissure when broaching and the broach is less likely to leave plastic debris in the bone. The combination of softer plastic material for the frame member 110 combined with the high-strength metal material for the panels 120 can make the broaches cheaper and lighter, while maintaining the broaches' high cutting performance.

In one exemplary embodiment, FIG. 22B shows the cross-sectional view of the broach 100. As depicted, the plurality of metal panels 120 can be circumferentially coupled to the frame member 110, which can have a hollow structure. The panels 120 can be formed using stamped punching and cutting technique, and the frame member 110 can be constructed using injecting molding technique.

As shown in FIG. 21, each broach 100, 200, 300 can have a corresponding proximal end 102, 202, 302 and a distal end 104, 204, 304. For each broach 100, 200, 300, a corresponding longitudinal length L1, L2, L3 can be defined between the respective proximal end 102, 202, 302 and the distal end 104, 204, 304. In certain embodiments, the broach 200 can have a larger longitudinal length than the first broach 100 (i.e., L2>L1), and the broach 300 can have a larger longitudinal length than the second broach 200 (i.e., L3>L2).

In some embodiments, each broach 100, 200, 300 can have a corresponding base 106, 206, 306 at the proximal end 102, 202, 302 of the broach. For each broach 100, 200, 300, the corresponding base 106, 206, 306 can have the maximum radial cross-sectional area. In certain embodiments, the base 206 of the second broach can have a larger radial cross-sectional area than the base 106 of the first broach, and the base 306 of the third broach can have a larger radial cross-sectional area than the base 206 of the second broach.

In addition, for each broach 100, 200, 300, the radial cross-sectional area of the broach can progressively increase from the distal end 104, 204, 304 to the base 106, 206, 306 so as to form a tapered shape near the distal end.

Each of the broaches 100, 200, 300 can have a corresponding longitudinal lumen (not shown). The lumen can be formed and encircled by the frame member and the depth of the lumen can extend at least a half of the longitudinal length of the broach. In addition, each broach 100, 200, 300 can have a corresponding opening 110, 210, 310 at the proximal end 102, 202, 302 and above the respective longitudinal lumen in the broach. In some embodiments, the opening 110, 210, 310 can be internally threaded.

As shown in FIG. 21, each broach 100, 200, 300 can have a corresponding longitudinal axis 112, 212, 312. For each broach 100, 200, 300, a radial offset r1, r2, r3 can be defined between the center of the corresponding opening 110, 210, 310 and the corresponding longitudinal axis 112, 212, 312. In certain embodiments, the radial offset of the second broach can be larger than that of the first broach (i.e., r2>r1), and the radial offset of the third broach can be larger than that of the second broach (i.e., r3>r2).

For each broach 100, 200, 300, a corresponding maximum radial dimension R1, R2, R3 can be defined as the largest distance from the corresponding longitudinal axis 112, 212, 312 to the periphery of the corresponding base 106, 206, 306. In certain embodiments, the offset ratio r1/R1 of the first broach 100 the offset ratio r2/R2 of the second broach 200, and the offset ratio r2/R2 of the second broach 200 is smaller than the offset ratio r3/R3 of the third broach 300.

In certain embodiments, the radial offset (e.g., r1, r2, r3) of the openings and/or the corresponding offset ratios (e.g., r1/R1, r2/R2, r3/R3) can be proportional to the radial cross-sectional area of the base of the corresponding broach so that the opening on a larger base can have a larger radial offset and/or offset ratio.

Figure 23:
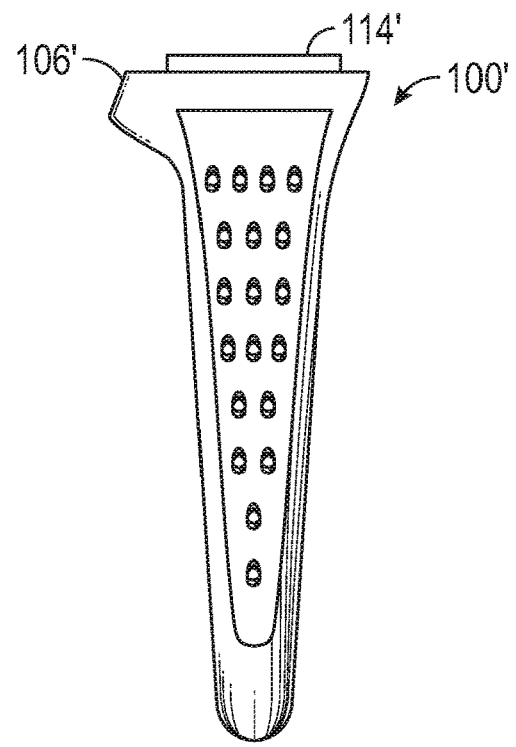
FIG. 23 shows a side elevation view of a broach, according to one embodiment.

In some embodiments, some of the broaches can have a platform at the proximal end. For example, FIG. 21 illustrates that the broach 200 can have a platform 214 extending proximally relative to the base 206, and the broach 300 can have a platform 314 extending proximally relative to the base 306. Note that in the embodiment depicted in FIG. 21, the smallest broach 100 has no platform, i.e., the base 106 can be a flat surface that tops the proximal end 102 of the first broach 100. However, in another embodiment as depicted in FIG. 23, the smallest broach 100' in the set can also have a platform 114' extending proximally relative to the base 106'.

In some embodiments, the platform 214, 314 can have a smaller radial cross-sectional area than the corresponding base 206, 306. In other embodiments, the platform 214, 314 can have the same radial cross-sectional area as the corresponding base 206, 306. In certain embodiments, the platform can be formed as an integral part of the frame member of the corresponding broach.

The platform can take a variety of structures and/or shapes so long as it can provide an elevated support for the trial neck as described more fully below. For example, the platform can have an encircled wall structure with a hollow interior that exposes the opening (e.g., 210, 310). Alternatively, the platform can have a body of cylindrical or elliptic cylindrical shape, and the opening (e.g., 210, 310) can extend through such body.

In some embodiments, the height of the platform 314 (along the longitudinal axis 312) for the third broach 300 can be larger than the height of the platform 214 (along the longitudinal axis 212) for the second broach 200. In some embodiments, when the first broach 100' also has a platform (e.g., FIG. 23), the height of the platform 214 for the second broach 200 can be larger than the height of the platform 114' of the first broach 100'.

Generally, the height of the platforms can range between 0 mm and about 4 mm. In certain embodiments, the height of the platform can be proportional to the longitudinal length of the corresponding broach so that a longer broach can have a higher platform. For example, in some embodiments, the height of the platform for the first broach 100 can range between 0 mm and about 2 mm, the height of the platform for the second broach 200 can range between about 0 mm and about 2 mm, and the height of the platform for the third broach 300 can range between about 0 mm and about 3 mm.

Driving Member

Figure 24A:
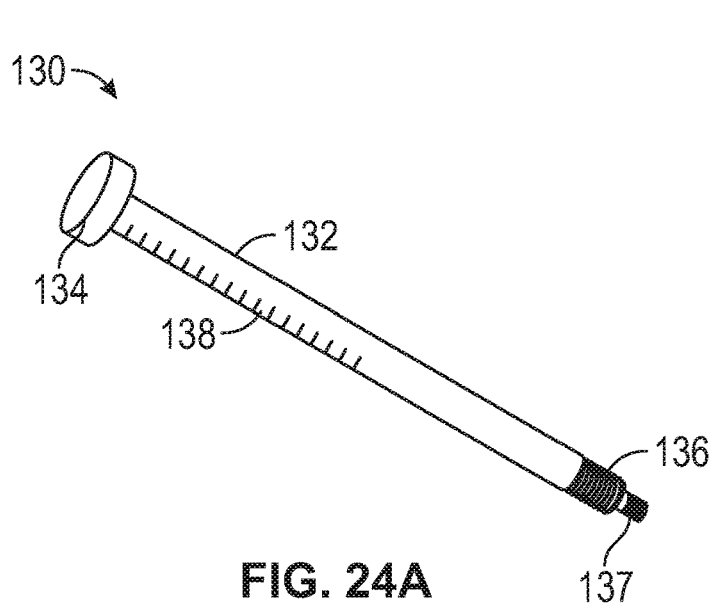
FIG. 24A shows a prospective view of a driving member, according to one embodiment.

In some embodiments, the system can also include a driving member 130. As shown in FIG. 24A, the driving member 130 can comprise an elongated rod 132 and an anvil top 134 coupled to one end of the rod 132, and the rod 132 can comprise a threaded distal portion 136 opposite the anvil top 134.

In some embodiments, a threaded distal tip 137 can protrude outwardly from the threaded distal portion 136. The distal tip 137 can have a cross-sectional smaller diameter than that of the distal portion 136. In some embodiments, the length of the distal tip 137 can be between about 2 mm and about 4 mm.

In some embodiments, the anvil top 134 and the rod 132 can be made of a metal material that has sufficient strength to withstand the impact from a mallet. In some embodiments, the rod 132 can include a calibrated length scale 138.

Figure 24B:
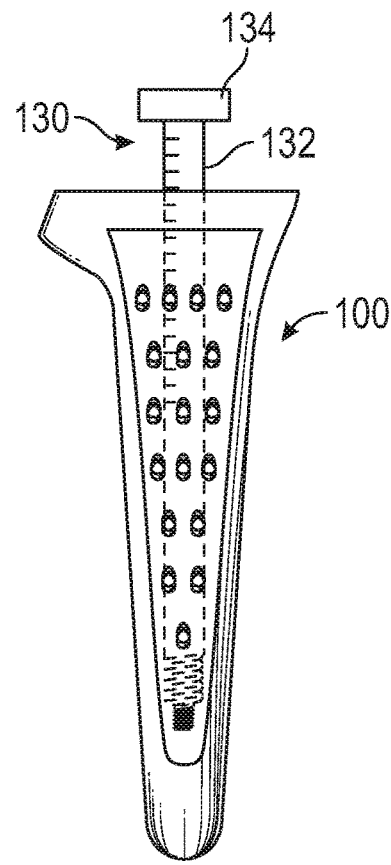
FIG. 24B illustrates coupling the driving member of FIG. 24A to a broach.

The driving member 130 can be used together with any of the broaches disclosed herein. As illustrated in FIG. 24B, the rod 132 of the driving member 130 can have a sufficiently small cross-sectional dimension so that it can be inserted through any of the openings 110, 210, 310 and into the longitudinal lumen of the corresponding broaches 100, 200, 300.

In some embodiments, the length of the rod 132 is larger than the depth of the lumen in any of the broaches 100, 200, 300. In some embodiments, the distal end of the lumen in each of the broaches can have a corresponding receiving member (not shown), which can be configured to couple to the threaded distal portion 136 and/or the threaded distal tip 137 of the rod 132.

Thus, for any of the broaches 100, 200, 300, the distal portion 136 and/or distal end 137 of the driving member 130 can be securely anchored at the distal end of the corresponding lumen, while the anvil top 134 and the driving member 130 can still remain outside the lumen. Accordingly, by impacting a mallet over the anvil top 134, the broach coupled to the rod 132 can be driven distally to create or size the femoral canal.

In some embodiments, the driving member 130 can be multi-functional. For example, besides coupling to the broaches, the distal portion 136 and/or distal tip 137 of the driving member 130 can also be threadably coupled to complimentarily arranged receiving members in other devices, such as a acetabular shell, a hollow tapered reamer, a trial femoral head, a femoral head impactor, a canal finder, a canal reamer, an osteotome, etc. For example, the threaded distal tip 137 can be configured to mate with a threaded central hole of the acetabular shell. In addition, a slide-on guide can be attached to the rod 132 of the driving member 130 for cup angle determination.

Trial Neck

The system can further include a trial neck 150 as shown in FIG. 25A. In some embodiments, the trial neck can comprise essentially of a plastic material. In some embodiments, the plastic material can be biodegradable.

The trial neck 150 can have a body portion 152 and a neck portion 154 extending laterally from the body portion 152. As described more fully below, the body portion 152 of the trial neck 150 can be releasably coupled to any of the proximal end 102, 202, 302 of the corresponding broaches 100, 200, 300.

In some embodiments, the body portion 152 of the trial neck 150 can comprise a channel 160 extending longitudinally through the body portion 152. In some embodiments, the channel 160 can be aligned with the opening 110, 210, 310 for each of the broaches 100, 200, 300.

In some embodiments, the system can include a coupling member 162 which can selectively couple the trial neck 150 to any of the broaches 100, 200, 300. In some embodiments, the coupling member 162 can be a screw-like device as depicted in FIG. 25B. For example, both the channel 160 in the trial neck 150 and the openings 110, 210, 310 of the broaches 100, 200, 300 can have internal threads that are configured to matingly engage with the external threads of the coupling member 162. Accordingly, the coupling member 162 can be threadably inserted through the channel 160 and into the opening 110, 210, 310, thus coupling the trial neck 150 to the corresponding broaches 100, 200, 300. Alternatively, the trial neck 150 can be releasably coupled to the broaches 100, 200, 300 by other means, such as clips, hooks, locks, keys, claps, snaps, buttons, buckles, etc.

In some embodiments, a medial end 156 of the neck portion 154 can comprise a head coupler 158, which can be configured to matingly couple to a complimentarily configured opening on a trial head, as described more fully below. In some embodiments, the head coupler 158 can be threaded.

For each broach 100, 200, 300, a lateral offset (LO) of the trial neck 150 can be defined as the distance between the medial end 156 of the neck portion 154 and the corresponding longitudinal axis 112, 212, 312 of the broach. As noted above, the opening of the broach can have different radial offset and/or offset ratio depending on the size of the broach. Thus, by respectively aligning the channel 160 with the openings 110, 210, 310 and then threadably coupling the trial neck 150 to the corresponding broaches 100, 200, 300, the lateral offset of the trial neck 150 coupled to the second broach 200 can be larger than that of the trial neck 150 coupled to the first broach 100, and the lateral offset of the trial neck 150 coupled to the third broach 300 can be larger than that of the trial neck 150 coupled to the second broach 100.

If the broach (e.g., 100) has no platform at the proximal end, then the trial neck 150 can rest directly on top of the base (e.g., 106) when coupled to the broach. If the broach (e.g., 200, 300) has a platform at the proximal end, then the trial neck 150 can rest on top of the platform (e.g., 214, 314) when coupled to the broach. As noted above, the height of the platform can vary depending on the size of the broach. Thus, by coupling the trial neck 150 to different broaches, the vertical elevation (VE) of the trial neck, measured as the distance from the medial end 156 of the trial neck 150 to the planar surface of the corresponding base can also vary. For example, the vertical elevation of the trial neck coupled to the second broach 200 can be larger than that of the trial neck 150 coupled to the first broach, and the vertical elevation of the trial neck 150 coupled to the third broach 300 can be larger than that of the trial neck 150 coupled to the second broach 200.

Thus, instead of stocking multiple trial necks of various size that respectively match different sized broaches as conventionally required, the disclosed system is simplified in that it allows only one trial neck to be selectively coupled to a plurality of broaches of different sizes for adjusting both the lateral offset and the vertical elevation of the trial neck. The system can, however, also have trial body/neck parts unique to each size broach, and the openings (110,210,310) would not necessarily vary in location on the broach body.

In some embodiments, the body portion 152 of the trial neck 150 can comprise an anchor member 164. Correspondingly, each of the broaches 100, 200, 300 can respectively comprise a lock member 108, 208, 308. The anchor member 164 can be configured to selectively matingly engage with the lock member 108, 208, 308 so as to resist rotational movement of the trial neck 150 relative to the corresponding broach 100, 200, 300.

In some embodiments, the anchor member 164 can be a lug protruding outwardly from the bottom surface of the body portion 152. The lock members 108, 208, 308 can be slots on the proximal end 102, 202, 302 of the respective broaches 100, 200, 300, and the lug can be so sized and shaped as to interference fit to the respective lock members 108, 208, 308. Alternatively, any other types of anchoring mechanism can be incorporated, such as key/key-hole, latch/catch, bolt/nut, etc. In some embodiments, the lock members 108, 208, 308 are arranged eccentric relative to the corresponding longitudinal axis 112, 212, 312 of the respective broaches.

Trial Head

The system can additionally include a trial head 170 as shown in FIG. 26A. The trial head 170 can have a partially spherical-shaped body 172 that is configured to be matingly engageable with the prepared acetabular socket previously prepared. In some embodiments, the partially spherical-shaped body 172 of the trial head 170 can be covered by an acetabular liner (not shown). The trial head 170 can have a coupling mechanism can is configured to removeably couple to the head coupler 158 of the neck portion 154.

In some embodiments, the coupling mechanism can include a recess (or channel) 176 underneath an opening 178 on the trial head 170. In some embodiments, the recess 176 can be internally threaded so that it is threadably mateable with an outer thread on the head coupler 158 of the neck portion 154. In some embodiments, the depth of the recess 176 can be configured to generally match the length of the head coupler 158 so that the head coupler 158 can be completed inserted into the recess 176 through the opening 178.

The system can further include a plurality of offset adjustment members 180. In some embodiments, the offset adjustment members 180 can be color-coded.

As depicted in FIG. 26A, the offset adjustment members 180 can be a set of washers with various thickness. In some embodiments, one or more washers 180 can be inserted into the recess 176 through the opening 178. When at least a washer 180 is inserted through the opening 178 and disposed at the floor 182 of the recess 176, the depth of the empty space in the recess 176 is reduced by the thickness of the washer 180. Thus, the head coupler 158 of the trial neck 150 cannot be fully inserted into the recess 176. Accordingly, when coupling the trial head 170 to the trial neck 150, the lateral offset of the trial head 170 can be at least partially determined by the thickness of the washer 180 inserted into the recess 176.

In alternative embodiments, the trial head 170 and the trial neck 150 can be coupled by other mechanisms than threading, such as latches, locks, clips, buckles, tapers, etc.

Additionally, the offset adjustment members 180 can take different forms than washers. For example, in certain embodiments (not shown), the offset adjustment members can be a set of screw nuts with various thickness that can be threadably coupled to the head coupler of the neck portion. Thus, the coupled screw nut can limit the extent to which the neck coupler of the trial head 170 can be coupled to the head coupler of the trial neck 150, thus limiting the lateral offset of the trial head 170.

Offset Handle

If the anterior approach is used for implanting the hip prosthesis, the system can further include an offset handle 190. Three exemplary embodiments of such handles 190a, 190b and 190c (collectively referred as 190) are respectively depicted in FIGS. 27A-27C.

Each handle 190a, 190b and 190c can have a distal section 192a, 192b and 192c and a proximal section 194a, 194b and 194c, respectively joined by an intermediate section 193a, 193b and 193c. A longitudinal axis 191a, 191b and 191c of the distal section can have a lateral offset from a longitudinal axis 195a, 195b and 195c of the respective proximal section. In some embodiments, the lateral offset between the proximal section and the distal section can range between about 15 mm and about 30 mm.

In the embodiments depicted in FIGS. 27A-27B, the proximal section 194a, 194b of the handle 190a, 190b can comprise an integrated anvil top 196a, 196b. In some embodiments, the integrated anvil top 196a, 196b can be made of a high-strength metal material, whereas the rest of the handle 190a, 190b can be made of a plastic material. In some embodiments, such plastic material can be biodegradable.

In the embodiment depicted in FIG. 27C, an impact member 196c can be removeably coupled to the proximal section 194c of the handle 190c. For example, the impact member 196c can include an anvil head 197h and a stem 197s extending from the anvil head 197h. The proximal section 194c of the handle 190c can have a recess 197r that is so sized and shaped to matingly engage, e.g., by means of threaded coupling or an interference fit, with the stem 197s of the impact member 196c.

In some embodiments, the impact member 196c can be made of a high-strength metal material, whereas the rest of the handle 190c can be made of a plastic material. In some embodiments, such plastic material can be biodegradable.

In the embodiments depicted in FIGS. 27A and 27C, the distal section 192a, 192c of the handle 190a, 190c can respectively comprise a distal neck 198a, 198c that is sized and shaped so as to be inserted into any of the openings 110, 210, 310 and into the longitudinal lumen of the corresponding broaches 100, 200, 300.

In the embodiment depicted in FIG. 27B, the distal section 192b of the handle 190b can comprise a passage 198b extending longitudinally through the distal section 192b. A complementary handle coupler 198b' can be so sized and shaped to be inserted through the passage 198b and into any of the openings 110, 210, 310 and into the longitudinal lumen of the corresponding broaches 100, 200, 300. In certain embodiments, the handle coupler 198b' can have an external thread that is mateable to an internal thread of the passage 198b as well as the internal thread of the openings 110, 210, 310.

Thus, the distal section 192a, 192b and 192c of the handle 190a, 190b, 190c can be selectively coupled to the proximal end 102, 202, 302 of the broaches 100, 200, 300. Accordingly, by impacting a mallet over the integrated anvil top 196a, 196b or the coupled impact member 196c, the broach coupled to the handle can be driven distally to create or size the femoral canal in the anterior approach.

In addition, the offset handle 190 can be multi-functional. For example, besides coupling to the broaches, the distal section of the offset handle can also be threadably coupled to complimentarily arranged receiving members in other devices, such as a canal finder, a canal reamer, an osteotome, etc.

Operating Procedure

Using the sterile kit including the flexible and/or multi-functional devices disclosed herein, the operating procedure for preparing prosthetic hip implantation can be significantly simplified.

Figure 28:
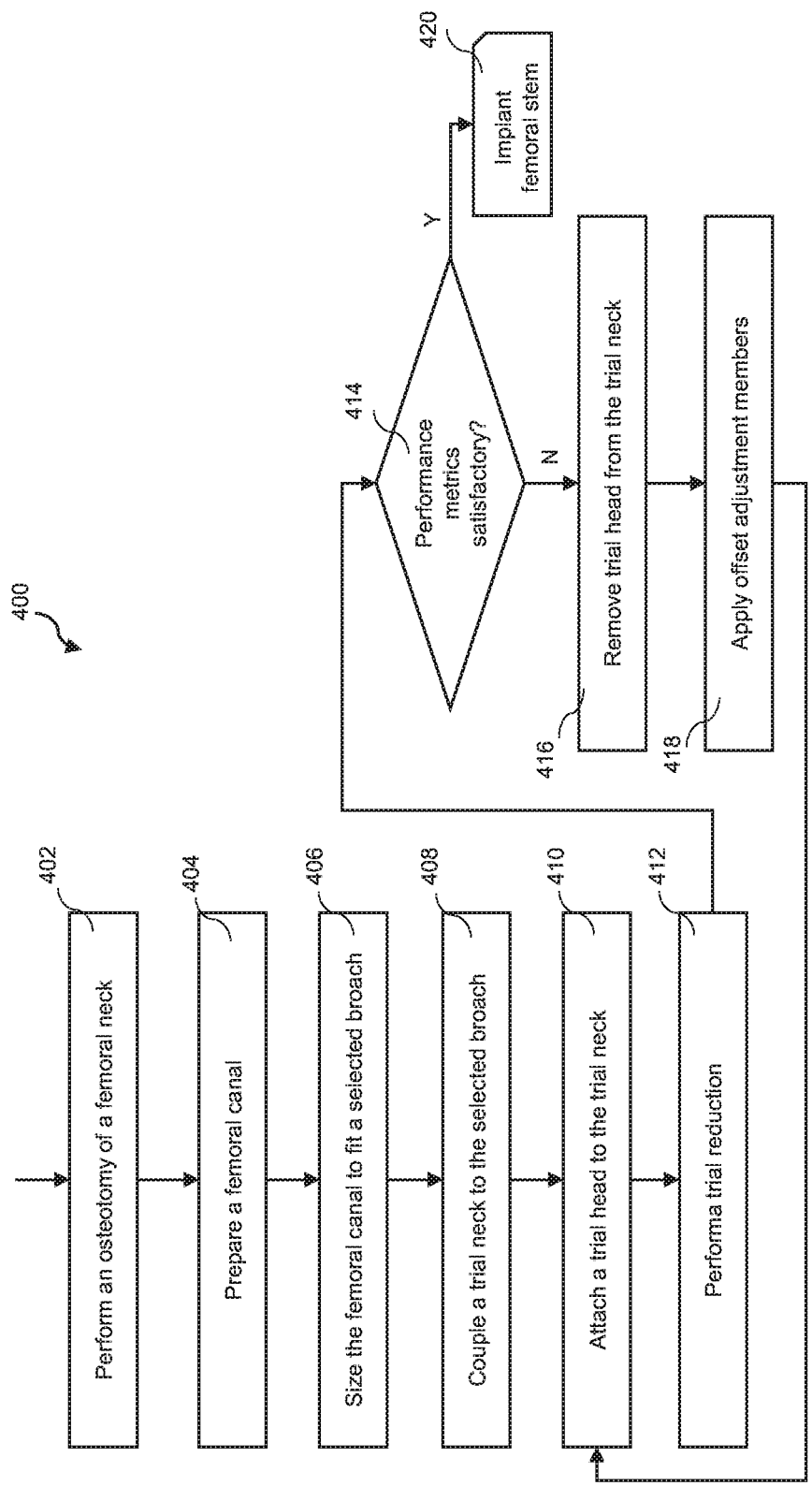
FIG. 28 shows a high-level flow diagram illustrating a procedure for preparing prosthetic hip implant, according to one embodiment.

FIG. 28 illustrates such a simplified procedure 400 according to one exemplary embodiment. At 402, an osteotomy of a patient's femoral neck can be performed. This can be achieved, for example, by activating an osteotome to remove a portion of a greater trochanter from a femur. In certain embodiments, the osteotome can include an attachment member which can be threadably coupled to the driving member 130 or an offset handle 190 if the anterior approach is used.

After osteotomy of the femoral neck, the leg of the patient can be internally rotated (for posterior approach) or externally rotated (for anterior approach to expose the cut surface of the femoral neck. Then at 404, a femoral canal can be prepared by creating a space inside the osteotomized femur. In certain embodiments, the space can be initially defined by using the smallest-sized broach in the pre-prepared sterile kit. For posterior approach, the driving member 130 can be coupled to such broach and a mallet can be used to impact the anvil top 134 of the driving member to drive the broach into the femur. For anterior approach, the offset handle 190 can be coupled to such broach and the mallet can be used to (e.g., by pounding on the integrated anvil top 196a, 196b or the impact member 196c) to drive the broach into the femur. In other embodiments, the space can be initially defined by using a canal finder and/or a canal reamer and then further enlarged by the smallest-sized broach.

At 406, the size of the created space can be compared to the size of a selected broach, which generally matches the size of a femoral stem to be implanted. In some circumstances, no further sizing of the femoral canal is needed when the space created by the smallest-sized broach is deemed sufficient to accommodate the femoral stem planned for implantation. In other circumstances, further sizing of the femoral canal can be conducted in order to further increase the space size to accommodate the femoral stem. The space size can be progressively increased by using one or more broaches of larger sizes, until the selected broach can press fit in the femoral canal. Similarly, each of the broaches can be coupled to the driving member 130 or the offset handle 190 (if anterior approach is used) and driven by the impacting forces of the mallet.

While keeping the selected broach press fit in the femoral canal, the trial neck 150 can be coupled to the selected broach at 408, for example, by inserting the coupling member 162 through the channel 160 of the trial neck 150 and into the opening of the selected broach.

Then, at 410, the trial head 170 can be attached to the trial neck 150, for example, by coupling the threaded opening 178 of the trial head 170 to the threaded neck portion 154 of the trial neck 150. In some embodiments, the lateral offset of the trial head can be adjusted by using the offset adjustment member 180, for example, by inserting one or more washers into the threaded opening 178 of the trial head 170 before coupling the trial head 170 to the trial neck 150.

Then trial reduction can be performed at 412 by assessing one or more performance metrics. The goal of the trial reduction is to ensure equal leg length while maintaining or increasing the lateral distance between patient's femur and pelvis. In some embodiments, the performance metrics can include any one or more of the parameters such as leg length, leg offset, leg stability, leg tension, etc.

At 414, the measured performance metrics are compared to a set of predefined criteria to evaluate if the trial reduction is satisfactory.

If the trial reduction does not satisfy the set of predefined criteria, then further adjustment is needed. For example, at 416, the trial head 170 can be removed from the neck portion 154 of the trial neck 150.

Then, at 418, the lateral offset of the trial head 170 can be adjusted through the offset adjustment member 180. For example, the lateral offset can be increased by inserting one or more washers into the threaded opening 178 of the trial head 170, or by replacing an inserted narrower washer with a wider washer. Conversely, the lateral offset can be decreased by removing one or more washers from the threaded opening 178 of the trial head 170, or by replacing an inserted wider washer with a narrow washer.

After adjusting the lateral offset, the process can return to 410 by reattaching the trial head 170 to the trial neck 150. The process can then be repeated by performing the trial reduction, reassessing the performance, and readjusting the lateral offset of the trial head 150 until the trial reduction satisfies the set of predefined criteria.

At 420, formal femoral implant can be performed after the trial reduction is determined to be satisfactory. The selected broach, together with the coupled trial neck 150 and the trial head 170, can be removed from the femoral canal. Then the femoral stem can be press fit into the femoral canal, and other formal implantation procedures can be performed.

Figure 29:
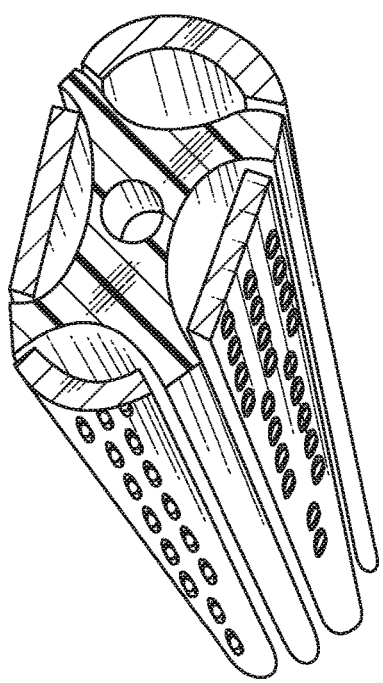
FIG. 29 shows a perspective view of a broach formed with stamped panels and a molded plastic frame.

FIG. 29 shows a perspective view of a broach formed with stamped panels and a molded plastic frame. The method of forming the broach with stamped panels can be the same general method as those disclosed above in, for example, FIGS. 11A-17C. In particular, the broach can be formed of stamped cutting panels that are secured to a injection molded plastic frame.

Figure 30A:
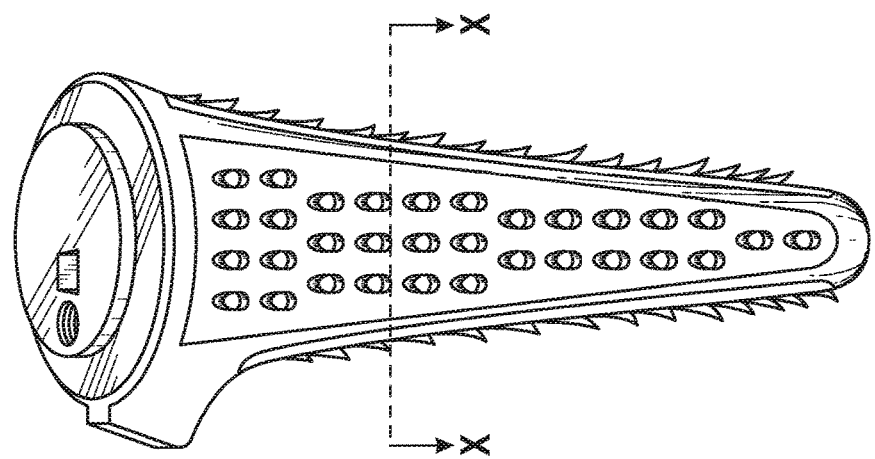
FIG. 30A illustrates a perspective side view of a broach formed with stamped panels and a molded plastic frame.
Figure 30D:
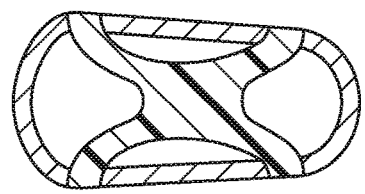
FIG. 30B-30D illustrate various cross-sectional designs of the broach of FIG. 30A, taken along line X-X.
Figure 30C:
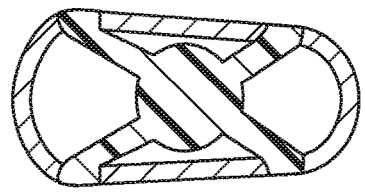
Figure 30B:
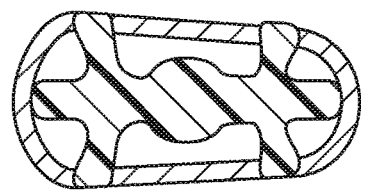

Various frames can be used. For example, FIG. 30A illustrates a perspective side view of a broach formed with stamped panels and a molded plastic frame and FIGS. 30B-30D illustrate various cross-sectional designs of the broach of FIG. 30A taken along line X-X.

In some embodiments, the broach is constructed with a plurality of stamped panels (e.g., 4) that are positioned between adjacent "legs" of the molded frame. The molded frame can have a centrally-extending portion that extends generally along a longitudinal center axis of the broach. A plurality of panel support members (e.g., "legs") extend from the centrally-extending portion and can generally extend along the length of the centrally-extending portion to provide a supporting structure for panels.

Figure 31E:
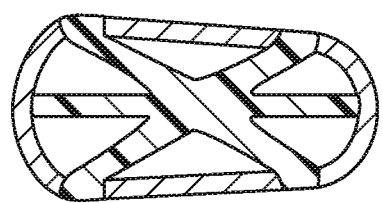
FIG. 31B-31E illustrate various cross-sectional designs of the broach of FIG. 31A, taken along line X-X.
Figure 31D:
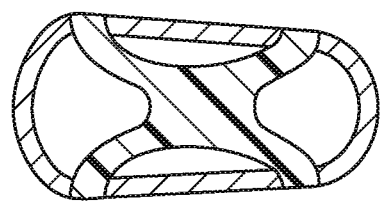
Figure 31C:
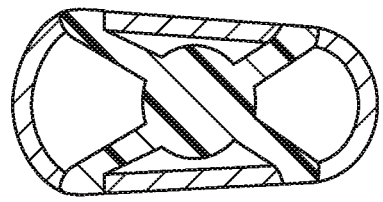
Figure 31B:
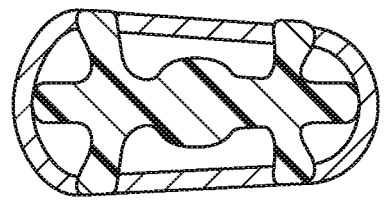
Figure 31A:
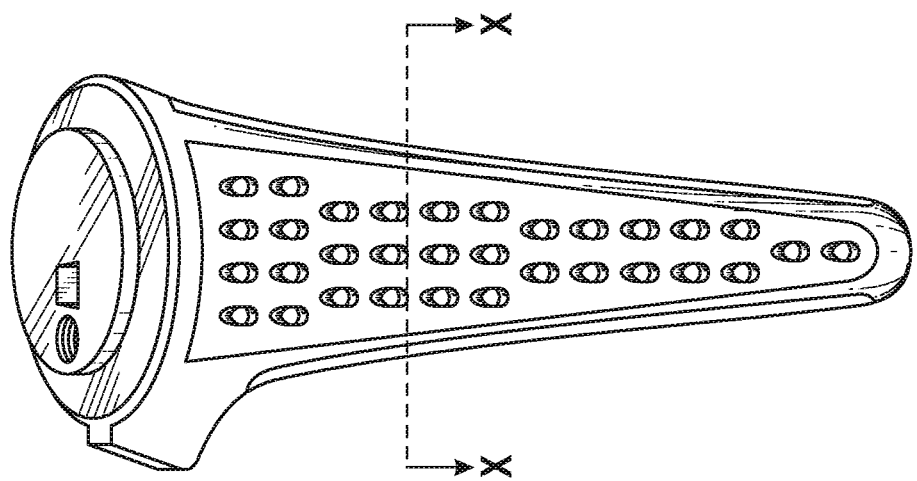
FIG. 31A illustrates a perspective side view of a broach formed with stamped panels and a molded plastic frame.

FIG. 31A illustrates a perspective side view of a broach formed with stamped panels and a molded plastic frame. As shown in FIGS. 30A and 31A, the panel support members can extend outwardly between adjacent panel members such that the molded plastic frame is exposed around the circumference of the broach.

FIG. 31B-31E illustrate various cross-sectional designs of the broach of FIG. 31A, taken along line X-X. The panel support members can only extend at locations between the adjacent panels (e.g., FIGS. 30C, 30D, 31C, 31D). Or, in other embodiments, one or more additional panel support members can be provided to provide intermediate support to a panel secured to the molded frame. For example, FIGS. 30B, 31B, and 31E illustrate embodiments where one or more additional panel support members extend and engage with a panel (near a central area of the span of the panel) to provide additional structure support to the panel.

In view of the many possible embodiments to which the principles of the disclosed may be applied, it should be recognized that the illustrated embodiments are only examples and should not be taken as limiting the scope of the claimed subject matter. Rather, the scope of the claimed subject matter is defined by the following claims and their equivalents.

We claim:

1. A broach for preparing prosthetic hip implantation, the broach comprising:
   a non-metal frame member and a plurality of metal panels circumferentially coupled to the frame member;
   wherein each panel comprises a plurality of cutting teeth, each tooth comprising a cutting hole on the panel and a cutting edge projecting radially outwardly from the cutting hole, and the cutting edges of the plurality of cutting teeth are spaced apart from one another along the panel;
   wherein the frame member comprises a plurality of grooves adjacent to the plurality of cutting teeth of the plurality of panels so as to provide pathways for bone debris to flow through inwardly when the plurality of cutting teeth are urged against and cut a bone tissue;
   wherein a proximal end of broach comprises a base, and a radial cross-sectional area of the broach progressively increases from a distal end of the broach to the base which has a maximum area; and
   wherein the proximal end of the broach comprises an opening above a longitudinal lumen enclosed by the frame member.

2. The broach of claim 1, wherein the longitudinal lumen comprises a threaded portion configured to receive a driving member.

3. The broach of claim 1, wherein the opening is sized to receive a coupling device to secure a trial neck to the proximal end of the broach.

4. The broach of claim 1, wherein the base defines a top surface of the proximal end of the first broach.

5. The broach of claim 1, further comprising a trial neck and a coupling member, the coupling member being configured to be inserted into a channel in the trial neck and into the opening in the broach to secure the trial neck to the first broach.

6. The broach of claim 5, wherein the trial neck comprises a neck portion and a body portion, the body portion of the trial neck comprising an anchor member, and the proximal end of the broach comprising a lock member sized to engage with the anchor member of the trial neck,
   wherein the anchor member is configured to selectively mate and engage with the lock member so as to resist rotational movement of the trial neck relative to the broach.

7. The broach of claim 6, wherein the anchor member comprises a lug extending distally from the body portion of the trial neck, and the lock member comprises a slot on the proximal end of the broach,
   wherein the lug is so sized and shaped as to interference fit to the lock member.

8. The broach of claim 7, wherein a medial end of the neck portion comprises a threaded segment, the threaded segment being configured to couple and mate to a complimentarily threaded opening on a trial head,
   wherein a depth of the coupling can be adjusted by one or more washers inserted into the trial head or around a base of the neck portion.

* * * * *